US009410968B2

(12) United States Patent
Meyer et al.

(10) Patent No.: US 9,410,968 B2
(45) Date of Patent: Aug. 9, 2016

(54) BIOMARKERS FOR ACUTE KIDNEY INJURY

(75) Inventors: Evelyne Meyer, Merelbeke (BE); Bert Maddens, Melle (BE)

(73) Assignee: UNIVERSITEIT GENT, Ghent (BE)

( * ) Notice: Subject to any disclaimer, the term of this patent is extended or adjusted under 35 U.S.C. 154(b) by 41 days.

(21) Appl. No.: 14/006,991

(22) PCT Filed: Mar. 29, 2012

(86) PCT No.: PCT/EP2012/055592
§ 371 (c)(1),
(2), (4) Date: Sep. 24, 2013

(87) PCT Pub. No.: WO2012/136548
PCT Pub. Date: Oct. 11, 2012

(65) Prior Publication Data
US 2014/0017702 A1 Jan. 16, 2014

(30) Foreign Application Priority Data

Apr. 4, 2011 (EP) ..................................... 11160965

(51) Int. Cl.
*G01N 33/68* (2006.01)
(52) U.S. Cl.
CPC ...... *G01N 33/6893* (2013.01); *G01N 2333/924* (2013.01); *G01N 2800/347* (2013.01)
(58) Field of Classification Search
None
See application file for complete search history.

(56) References Cited

U.S. PATENT DOCUMENTS

| | | | | |
|---|---|---|---|---|
| 5,935,798 | A * | 8/1999 | Price et al. | ............ 435/7.23 |
| 7,229,770 | B1 | 6/2007 | Price et al. | |
| 2002/0031793 | A1 * | 3/2002 | Price et al. | ............ 435/7.23 |
| 2010/0183520 | A1 | 7/2010 | Ramesh | |
| 2013/0035290 | A1 | 2/2013 | Elias | |
| 2014/0200184 | A1 | 7/2014 | Elias | |

FOREIGN PATENT DOCUMENTS

| | | |
|---|---|---|
| EP | 1112497 B1 | 2/2008 |
| WO | WO 00/19206 A1 | 4/2000 |
| WO | WO 2009/141359 | 11/2009 |
| WO | WO 2010/090834 A2 | 8/2010 |
| WO | WO 2012/136548 A1 | 10/2012 |

OTHER PUBLICATIONS

Seol et al., Serum Levels of YKL-40 and Interleukin-18 and Their Relationship to Disease Severity in Patients with Preeclampsia, Journal of Reproductive Immunology, Jan. 1, 2009, pp. 183-187, vol. 79, No. 2, Elsevier Science, Ireland Ltd, IE.
Brix et al., YKL-40 in Type 2 Diabetic Patients with Different Levels of Albuminuria, European Journal of Clinical Investigation, Dec. 16, 2010, pp. 589-596, vol. 41, No. 6, Blackwell Publishing Ltd, GBR.
PCT International Search Report, PCT/EP2012/055592 dated Apr. 25, 2012.
Hall et al., "A comparison of alternative serum biomarkers with creatinine for predicting allograft function after kidney transplantation." 2011, Transplantation 91:48-56.
Lee et al., "Role of chitin and chitinase/chitinase-like proteins in inflammation, tissue remodeling, and injury." 2011, Annu Rev Physiol 73:479-501.
Muhlberger et al., "Biomarkers in renal transplantation ischemia reperfusion injury." 2009, Transplantation 88:S14-19.
Bojesen et al., "Plasma YKL-40 levels in healthy subjects from the general population." 2011l Clin Chim Acta 412:709-712.
Chupp et al., "A chitinase-like protein in the lung and circulation of patients with severe asthma." 2007, N Engl J Med 357:2016-2027.
Elias et al., "Chitinases and chitinase-like proteins in T(H)2 inflammation and asthma." 2005, J Allergy Clin Immunol 116:497-500.
Fontana et al., "Serum fibrosis markers are associated with liver disease progression in non-responder patients with chronic hepatitis C." 2010, Gut 59:1401-1409.
Francescone et al., "Role of YKL-40 in the angiogenesis, radioresistance, and progression of glioblastoma." 2011l J Biol Chem. 286(17):15332-43.
Hall et al., "IL-18 and urinary NGAL predict dialysis and graft recovery after kidney transplantation." 2010, J Am Soc Nephrol21:189-197.
Hall et al., "Urine cystatin C as a biomarker of proximal tubular function immediately after kidney transplantation." 2011, Am J Nephrol 33:407-413.
Hall et al., Abstract, "A comparison of alternative serum biomarkers with creatinine for predicting allograft function after kidney transplantation." 2011, Transplantation 91:48-56.
Jang et al., "The interaction between ischemia-reperfusion and immune response in the kidney." 2009, J Mol Med 87:859-864.
Lee et al., 2009, "Role of breast regression protein 39 (BRP-39)/chitinase 3-like-1 in Th2 and IL-13-induced tissue responses and apoptosis." The Journal of Experimental Medicine 206: 1149-1166.
Lee et al., "Distinct macrophage phenotypes contribute to kidney injury and repair." 2011, J Am Soc Nephrol 22:317-326.
Lee et al., Abstract, "Role of chitin and chitinase/chitinase-like proteins in inflammation, tissue remodeling, and injury." 2011, Annu Rev Physiol 73:479-501.
Muhlberger et al., Abstract, "Biomarkers in renal transplantation ischemia reperfusion injury." 2009, Transplantation 88:S14-19.
Rathcke and Vestergaard, "YKL-40—an emerging biomarker in cardiovascular disease and diabetes." 2009, Cardiovasc Diabetol 8:61.
Shackel et al., "Novel Differential gene expression in human cirrhosis detected by suppression subtractive hybridization." 2003, Hepatology 38:577-588.
Thom et al., "Elevated pretreatment serum concentration of YKL-40—An independent prognostic biomarker for poor survival in patients with metastatic nonsmall cell lung cancer." 2010, Cancer 116:4114-4121.

(Continued)

*Primary Examiner* — Brian J Gangle
*Assistant Examiner* — Andrea McCollum
(74) *Attorney, Agent, or Firm* — TraskBritt, P.C.

(57) ABSTRACT

Disclosed is an animal model that can be used, among other things, to generate biomarkers for the prognosis and/or diagnosis of acute kidney injury, more specifically sepsis-induced acute kidney injury. Disclosed are three such biomarkers. The disclosure specifically relates to human chitinase 3-like protein 1 for use as a biomarker.

2 Claims, 17 Drawing Sheets

(56) References Cited

OTHER PUBLICATIONS

Maddens et al., Severity of sepsis-induced acute kidney injury in a novel mouse model is age dependent, Crit Care Med, 2012, pp. 2638-2646, vol. 40, No. 9.

Maddens et al., Chitinase-like Proteins are Candidate Biomarkers for Sepsis-induced Acute Kidney Injury, Molecular & Cellular Proteomics, 2102, pp. 1-13, vol. 11.6.

Maddens, B., Urinary Biomarkers for Infection-Associated Kidney Injury: (Pre)Clinical Discovery and Validation, Dissertation submitted to Universiteit Gent, 2011.

Maddens, B., Urine Gel-Free Proteome Analysis in a Novel Aged Mouse Model of Sepsis-Induced Acute Kidney Injury, Abstract, at least as early as Apr. 8, 2011.

Maddens, B., Urine gel-free proteome analysis in a novel aged mouse model of sepsis-induced acute kidney injury, Poster, presented at the World Congress of Nephrology, Apr. 8-12, 2011, Vancouver, Canada.

* cited by examiner

Urinary CHI3L3

A. Kidney CHI3L3 (beta-actin as loading control)

B. Urine and kidney SPR

BIOMARKERS FOR ACUTE KIDNEY INJURY

CROSS-REFERENCE TO RELATED APPLICATIONS

This application is a national phase entry under 35 U.S.C. §371 of International Patent Application PCT/EP2012/055592, filed Mar. 29, 2012, designating the United States of America and published in English as International Patent Publication WO2012/136548 A1 on Oct. 11, 2012, which claims the benefit under Article 8 of the Patent Cooperation Treaty to European Patent Office Application Serial No. 11160965.7, filed Apr. 4, 2011.

TECHNICAL FIELD

The application relates generally to biotechnology and medicine. Among other things, disclosed is an animal model that can be used, among other things, to generate biomarkers for the prognosis and/or diagnosis of acute kidney injury, more specifically sepsis-induced acute kidney injury. Specifically disclosed are three such biomarkers. It specifically relates to human chitinase 3-like protein 1 for use as a biomarker.

BACKGROUND

Sepsis and acute kidney injury (AKI) can account for up to 37% (Vincent et al.) and 39% (Fonseca Ruiz et al.) of critically ill patients hospitalized in intensive care units (ICU), respectively, and therefore represent major health challenges. Despite extensive research and recent advances in supportive care and diagnostic tools (Lever A; Reinhart K et al.), severe sepsis and septic shock remain associated with unacceptably high mortality rates (25-70%). In this context, AKI is a frequent (Klenzak; Rangel-Frausto M S et al.) and important complication of sepsis in critically ill patients (Mehta et al.), leading to an especially high mortality rate (Russell et al., 2000).

Different mouse models for sepsis have been developed, either to study the pathophysiology or to function as a preliminary testing ground. Injection of endotoxin (LPS), infection with exogenous bacteria and disruption of the host-barrier as in cecal ligation and puncture (CLP) or colon ascendens stent peritonitis (CASP), are among the most commonly studied mouse models for sepsis. Their representativeness for human sepsis has intensively been discussed (Buras et al., 2005; Rittirsch et al., 2007; Dyson and Singer, 2009). In general, clinically relevant sepsis models should incorporate a focus of infection as septic origin (Deitch, 1998). Although consecutive surgical focus sanitation is the most important therapeutic principle in humans, removal of the source of infection in CLP and CASP models to study recovery of sepsis-induced AKI is seldom reported (Maier et al., 2004; Hubbard et al., 2005; reviewed in Zanotti-Cavazzoni, 2009).

A need for better preclinical animal models of acute renal failure was expressed in the Second International Consensus Conference of the Acute Dialysis and Quality Initiative Group (Bellomo et al., 2004). Indeed, sepsis models often have difficulties in reproducing AKI since they are either too aggressive with consequent death or the insult is too mild to cause AKI (Barrera et al., 2010; reviewed in Doi et al., 2009 and Langenberg et al., 2008). In addition, supportive therapy, comorbidities and the effect of age are rarely included in those models, despite the fact that these aspects are of major clinical relevance for human sepsis (Dejager et al., 2011). Recently, a few complex extensions of the current animal models of human sepsis including aged mice or mice with pre-existing renal dysfunction (two-hit models) have been described as useful for detection of potential therapeutic targets (Doi et al., 2009; Fink, 2008; Holly et al., 2006; Miyaji et al., 2003). Importantly, these adapted models lead to increased reproducibility of AKI and provided additional insights into septic AKI mechanisms.

In addition to a need for better preclinical animal models, there is further an urgent need for early prediction, prognosis and/or diagnosis of sepsis, of AKI and, more specifically, of sepsis-induced AKI. Indeed, early and specific diagnosis of AKI is of benefit for the prevention and targeted intervention of sepsis-induced AKI (Soni et al., 2009). Recently, several promising biomarkers for AKI have been identified (e.g., IL-18, NGAL, KIM-1, CysC, L-FABP) and validated in clinical settings, yet few clinical studies have included septic patients (reviewed in Bagshaw et al., 2007). Although some of these biomarkers hold promise for real-time indication, early prediction or prognostic information of AKI (Haase et al., 2011; Devarajan, 2010), their specificity for diagnosis of sepsis-induced AKI still requires further study (Siew et al., 2009; Martensson et al., 2010; Nejat et al., 2010; Siew et al., 2010; Doi et al., 2010).

AKI may be due to other causes than sepsis. Indeed, it has been shown that in adults who underwent cardiac surgery, about 35% of patients developed AKI. Other risks for AKI include critical illness, circulatory shock, burns, trauma, major noncardiac surgery, nephrotoxic drugs or radiocontrast agents ... (KDIGO consortium, Kidney International supplement 2, 2012). This KDIGO statement confirms the urgent need for early detection, prognosis and/or diagnosis of AKI due to any cause.

Chitinases and chitinase 3-like (CHI3L) proteins are members of the mammalian chitinase family (reviewed in Lee et al., 2011). CHI3L3 is a mouse specific chitinase 3-like protein and is strongly related to the human CHI3L protein 1 with which it has considerable sequence homology (Jin et al., 1998; Guo et al., 2000).

Hattori et al. (2009) suggested that serum concentrations of CHI3L1 (YKL-40) in human septic patients might be useful for severity grading of renal failure. However, elevated serum concentrations of CHI3L1 have also been reported in humans with certain types of solid tumors (reviewed in Lee et al.; 2011) and with other inflammatory conditions, such as inflammatory bowel disease (Bernardi et al., 2003), liver fibrosis (Johansen et al., 2000) and cardiovascular disease (Rathcke et al., 2010). Therefore, increased serum concentrations of CHI3L1 lack specificity and cannot diagnose sepsis and/or renal failure when concomitant diseases are present.

Acidic mammalian chitinase (CHIA, ACMase) (Lee et al., 2011), another member of the chitinase family, and sepiapterine reductase (Ichinose et al. 1991, Biochem Biophys. Res. Comm. 183) have not been described in relation to sepsis and/or AKI.

SUMMARY OF DISCLOSURE

Provided is an alternative animal model for sepsis by uterine ligation and inoculation (ULI) of a micro-organism, such as *Escherichia coli* (*E. coli*), a part of the micro-organism or a metabolite derived from the micro-organism resulting in septic AKI. Moreover, aged and old postmenopausal animals have more severe forms of sepsis and AKI than young animals after the same septic insult. In vivo imaging documents that ULI is followed by a persistent challenge of the body with the micro-organism. Animals with sepsis-induced AKI have a higher load of micro-organisms, significantly increased plasma cyto- and chemokine concentrations and more severe hypothermia than animals without AKI. Activation of caspase-1 and -7 and apoptosis of renal tubular cells is detected in animals with AKI, but not in animals without AKI. Finally, removal of the uterine infectious focus is studied in young animals and initiates recovery from sepsis and sepsis-induced AKI.

Further provided are biomarkers for sepsis, and more specifically, specific for sepsis-induced AKI or for AKI as such, by comparison of the proteomes of subjects with and without sepsis, and more specifically, with and without AKI, and/or by comparison of the proteomes of septic subjects both before and after sepsis, or, of subjects both before and after AKI. Provided as markers are chitinase-3-like protein 1 (CHI3L1), acidic mammalian chitinase (CHIA) (both members of the chitinase family) and sepiapterin reductase (SPR) and specifically relates to the usage of CHI3L1 as marker for AKI. Indeed, disclosed is the detection of CHI3L1 and -3 only in urine of mice with experimental sepsis in severe stages of AKI (tubular damage score or TDS≥4), and of CHIA only in urine of mice with experimental sepsis with AKI (tubular damage score or TDS≥2) and not in urine of septic mice without AKI, indicating that the urinary presence of these proteins is not merely the result of glomerular plasma filtration. Hence and surprisingly, disclosed is that these proteins are specific urinary markers for sepsis-induced AKI and AKI as such. Moreover, specifically disclosed are increased levels of CHI3L1 in urine of septic patients with AKI and not in septic patients without AKI. In addition, septic mice with AKI had a different immuno-reactive protein band pattern of CHI3L3 in kidney homogenates than sham-inoculated control mice and septic mice without AKI. These results therefore strongly indicate that urinary CHI3L1 (and -3) and/or CHIA and/or SPR reflect an ongoing local process in the kidneys of septic mice with severe stages of AKI. In other words, the presence of CHI3L1 and/or CHIA and/or SPR in a urine sample of a test-subject provides a specific indication for having or being at risk of sepsis-induced AKI or AKI as such. Moreover, the presence of CHIA and or SPR in a sample of a test-subject provides a specific indication for having or being at risk of sepsis and/or sepsis-induced AKI or AKI as such.

First provided is an animal model for sepsis-induced AKI characterized in that a uterine horn of the animal has been ligated and that the resulting ligated horn is inoculated with a micro-organism, a part of the micro-organism or a metabolite derived from the micro-organism.

The term "animal" refers to any animal or mammal and/but more specifically to rodents, such as rats and mice. Even more specific, but non-limiting, examples of mice are the mice strains C57BL/6 and CD-1. Other examples of "animals" are animals having a non-functional gene (i.e., the so-called knock-out strains) encoding for the proteins caspase 1, -3 and/or -7, interleukin 1beta and/or Toll-like Receptors.

Therefore, disclosed is an animal model, as described above, wherein the animal is a rodent and more specifically wherein the animal is a mouse.

Further specifically disclosed is an animal model, as described above, wherein the uterine horn is one uterine horn ligated cranial to the bifurcation uteri. Both the left and/or right uterine horn can be ligated. Alternatively, no ligation is needed and the complete uterus is inoculated with a micro-organism, a part of the micro-organism or a metabolite derived from the micro-organism and can thereafter be completely removed (i.e., hysterectomy).

The term "micro-organism" refers to Gram-negative bacteria, such as *E. coli*, Gram-positive bacteria, such as *Staphylococcus aureus* and bacterial species belonging to the genus *Streptococcus*, to fungi and to viruses. Specific, but non-limiting, examples of "metabolites" are endotoxins and/or exotoxins, such as lipopolysaccharide (LPS), enterotoxins, alpha- and betatoxins and streptolysin.

Further provided is an animal model, as described above, wherein the micro-organism is a Gram-negative bacterium belonging to the genus *Escherichia*.

Also disclosed is an in vitro method for the prediction, prognosis and/or diagnosis of sepsis and/or sepsis-induced AKI, or AKI in a test subject comprising:
  measuring the level of acidic mammalian chitinase and/or sepiapterin reductase in a biological sample taken from the test subject, and
  comparing the level of acidic mammalian chitinase and/or sepiapterin reductase with a reference level of acidic mammalian chitinase and/or sepiapterin reductase obtained from a sample from a healthy subject or a subject with sepsis without sepsis-induced AKI, wherein
  an increased level of acidic mammalian chitinase and/or sepiapterin reductase chitinase in a sample of the test subject as compared to that of a sample of a healthy subject or a subject with sepsis without sepsis-induced AKI indicates that the test subject has or is at risk of having sepsis and/or sepsis-induced AKI, or AKI.

Described is an in vitro method for the prediction, prognosis and/or diagnosis of sepsis-induced AKI or AKI, in a test subject comprising:
  measuring the level of chitinase 3-like protein 1, acidic mammalian chitinase and/or sepiapterin reductase in a urine sample taken from the test subject, and
  comparing the level of chitinase 3-like protein 1, acidic mammalian chitinase and/or sepiapterin reductase with a reference level of chitinase 3-like protein 1, acidic mammalian chitinase and/or sepiapterin reductase obtained from a urine sample from a healthy subject, or more specifically, of a septic subject without AKI, wherein
  an increased level of chitinase 3-like protein 1, acidic mammalian chitinase and/or sepiapterin reductase in a urine sample of the test subject as compared to that of a urine sample of a healthy subject, or more specifically, of a septic subject without AKI indicates that the test subject has or is at risk of having sepsis-induced AKI or AKI.

Further described is an in vitro method for the prediction, prognosis and/or diagnosis of sepsis-induced AKI or AKI in a test subject comprising:
  measuring the level of chitinase 3-like protein 1 in a urine sample taken from the test subject, and
  comparing the level of chitinase 3-like protein 1 with a reference level of chitinase 3-like protein 1 obtained from a urine sample from a healthy subject without AKI or of a septic subject without AKI, wherein
  an increased level of chitinase 3-like protein 1 in a urine sample of the test subject as compared to that of a urine sample of a healthy subject without AKI or of a septic subject without AKI indicates that the test subject has or is at risk of having sepsis-induced AKI or having AKI.

BRIEF DESCRIPTION OF FIGURES

FIG. 6: B. Terminal deoxynucleotidyl transferase (Tdt)-mediated nick-end labeling (TUNEL) staining of formalin-fixed kidney sections. At 48 hours p.i. with PBS, apoptotic nuclei are rarely found (A, B), while with *E. coli*, apoptotic nuclei were predominantly found in tubules (C, D). Original magnification, ×200 (B) or ×400 (A, C, D).

DETAILED DESCRIPTION

Figure 1:
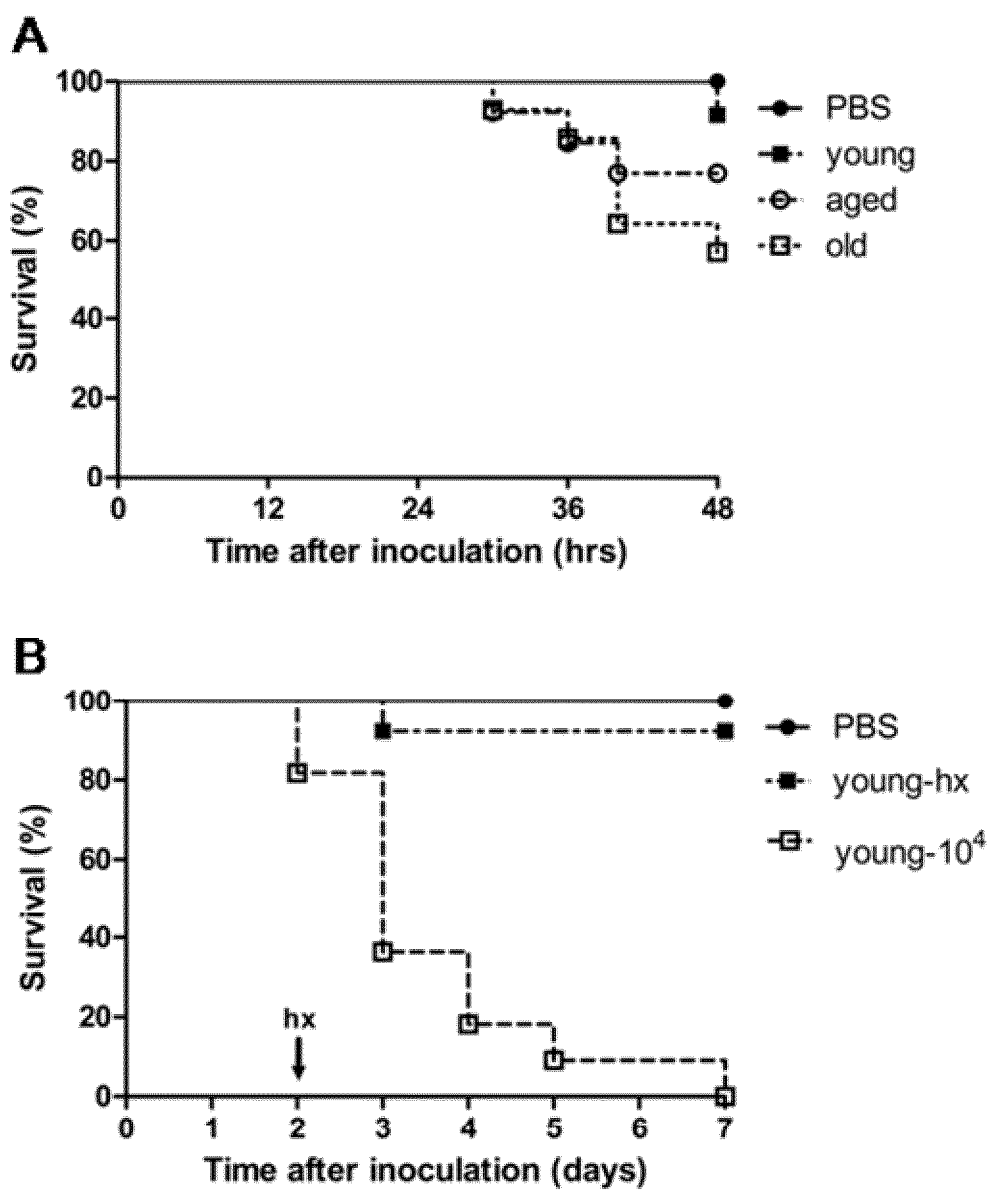
FIG. 1: Survival analysis after uterine ligation and inoculation (ULI) of *E. coli* in young (12 to 14 weeks), aged (46 to 48 weeks) and old (70 to 72 weeks) C57BL/6 mice and PBS-inoculated age-matched control mice. (A) Ageing mice are more prone to die after the same septic insult ($10^3$ CFU of *E. coli*). Survival at 48 hours was 100% in young, aged, and old mice inoculated with PBS. (B) Removal of the infectious focus at 48 hours after inoculation of $10^4$ CFU of *E. coli* in young mice (young-hx) prolongs survival. All young mice that underwent infection with $10^4$ CFU of *E. coli* (young-$10^4$) died within 7 days after ULI. The combined results of independent experiments are shown (n=15-17 for PBS, young, aged, old and young-$10^4$ mice, n=12 for young-hx mice).

The methods hereof refer, for example, to immunoassay technologies or mass spectrometric analysis methods, which are, for example, described in detail in WO 2009/141359, which is hereby incorporated by reference.

The term "chitinase 3-like protein" refers to members of the mammalian chitinase family (reviewed in Lee et al., 2011). CHI3L3 is a mouse specific chitinase 3-like protein and is strongly related to the human CHI3L protein 1 with which it has considerable sequence homology (Jin et al., 1998; Guo et al., 2000).

Human chitinase 3-like protein 1 has in the NCBI Reference Sequence Database (worldwide web at ncbi.nlm.nih.gov/protein) the accession number NP 001267.2 GI:144226251 and the following amino acid sequence (SEQ ID NO:1):

```
  1 mgvkasqtgf vvlvllqccs ayklvcyyts wsqyregdgs cfpdaldrfl cthiiysfan
 61 isndhidtwe wndvtlygml ntlknrnpnl ktllsvggwn fgsqrfskia sntqsrrtfi
121 ksvppflrth gfdgldlawl ypgrrdkqhf ttlikemkae fikeaqpgkk qillsaalsa
181 gkvtidssyd iakisqhldf isimtydfhg awrgttghhs plfrgqedas pdrfsntdya
241 vgymlrlgap asklvmgipt fgrsftlass etgvgapisg pgipgrftke agtlayyeic
301 dflrgatvhr ilgqqvpyat kgnqwvgydd qesvkskvqy lkdrqlagam vwaldlddfq
361 gsfcgqdlrf pltnaikdal aat
```

The terms "acidic mammalian chitinase" (Lee et al., 2011) refers to another member of the chitinase family and the term "sepiapterine reductase" refers to a protein, as described by, for example, by Ichinose et al. (1991, Biochem Biophys. Res. Comm: 183).

Acidic mammalian chitinase human has in the NCBI Reference Sequence Database (worldwide web at ncbi.nlm.nih.gov/protein) the accession number NP_970615.2 GI:133893286 (isoform c) and the following amino acid sequence (SEQ ID NO:2):

```
  1 mtklilltgl vlilnlqlgs ayqltcyftn waqyrpglgr fmpdnidpcl cthliyafag
 61 rqnneittie wndvtlyqaf nglknknsql ktllaiggwn fgtapftamv stpenrqtfi
121 tsvikflrqy efdgldfdwe ypgsrgsppq dkhlftvlvq emreafeqea kqinkprlmv
181 taavaagisn iqsgyeipql sqyldyihvm tydlhgsweg ytgensplyk yptdtgsnay
241 lnvdyvmnyw kdngapaekl ivgfptyghn filsnpsntg igaptsgagp agpyakesgi
```

```
-continued
301  wayyeictfl  kngatqgwda  pqevpyayqg  nvwvgydnik  sfdikaqwlk  hnkfggamvw 361  aidlddftgt  fcnqgkfpli  stlkkalglq  sasctapaqp  iepitaapsg  sgngsgssss 421  ggssggsgfc  avranglypv  annrnafwhc  vngvtyqqnc  qaglvfdtsc  dccnwa,
``` or has the accession number NP_068569.2 GI:42542398 (isoform a) and the following amino acid sequence (SEQ ID NO:3):

```
  1  mvstpenrqt  fitsvikflr  qyefdgldfd  weypgsrgsp  pqdkhlftvl  vqemreafeq 61  eakqinkprl  mvtaavaagi  sniqsgyeip  qlsqyldyih  vmtydlhgsw  egytgenspl 121  ykyptdtgsn  aylnvdyvmn  ywkdngapae  klivgfptyg  hnfilsnpsn  tgigaptsga 181  gpagpyakes  giwayyeict  flkngatqgw  dapqevpyay  qgnvwvgydn  iksfdikaqw 241  lkhnkfggam  vwaidlddft  gtfcnqgkfp  listlkkalg  lqsasctapa  qpiepitaap 301  sgsgngsgss  ssggssggsg  fcavrangly  pvannrnafw  hcvngvtyqq  ncqaglvfdt 361  scdccnwa
```

Sepiapterine reductase human has in the NCBI Reference Sequence Database (worldwide web at ncbi.nlm.nih.gov/protein) the accession number AAH17310.1 GI:16878218 and the following amino acid sequence (SEQ ID NO:4):

```
  1  megglgravc  lltgasrgfg  rtlapllasl  lspgsvlvls  arndealrql  eaelgaersg 61  lrvvrvpadl  gaeaglqqll  galrelprpk  glqrlllinn  agslgdvskg  fvdlsdstqv 121  nnywalnits  mlcltssvlk  afpdspglnr  tvvnisslca  lqpfkgwaly  cagkaardml 181  fqvlaleepn  vrvlnyapgp  ldtdmqqlar  etsvdpdmrk  glqelkakgk  lvdckvsaqk 241  llsllekdef  ksgahvdfyd  k
```

It is further clear that the latter terms also encompass fragments of CHI3L1, CHIA and/or SPR or functional variants thereof, which can be used as biomarkers in the in vitro methods hereof. The term "fragment" specifically refers to an amino acid sequence containing fewer amino acids than the amino acid sequences as depicted by SEQ ID NOS:1-4 and which can be used as biomarkers in the in vitro methods hereof. The term "variant" specifically refers to an amino acid sequence having at least 50% sequence identity, preferably having at least 51-70% sequence identity, more preferably having at least 71-90% sequence identity or most preferably having at least 91, 92, 93, 94, 95, 96, 97, 98 or 99% sequence identity with SEQ ID NOS: 1-4 or with a fragment thereof, and, which can be used as biomarkers in the in vitro methods hereof.

The term "test subject" refers to humans and animals, such as dogs, cats and horses.

The term "biological sample" refers any sample or biopsy or tissue, such as any tissue derived from the kidney, but specifically relates to any body fluid, such as blood, plasma, serum, saliva or, preferably, urine.

Therefore, and more specifically, the present invention provides for an in vitro method, as described above, wherein the biological sample is urine.

Described is a kit for the prediction, prognosis and/or diagnosis of sepsis, sepsis-induced AKI and/or AKI in a test subject comprising binding molecules for chitinase 3-like protein 1, acidic mammalian chitinase and/or sepiapterine reductase. Specifically described is the usage of a kit for the prediction, prognosis and/or diagnosis of sepsis, sepsis-induced AKI and/or AKI in a test subject comprising binding molecules for chitinase 3-like protein 1.

The term "kit" refers to any manufacture (e.g., a package or a container) comprising at least one reagent (e.g., an antibody, a protein, a small molecule, etc.) for performing an assay, which specifically detects the presence of chitinase 3-like protein 1, acidic mammalian chitinase and/or sepiapterine reductase. Positive and/or negative controls can be included in the kits to validate the activity and correct usage of reagents employed in accordance with the present invention. The design and use of controls is standard and well within the routine capabilities of those of ordinary skill in the art. The kit can be promoted, distributed, or sold as a unit for performing the methods or usages of the present invention. Additionally, the kits can contain a package insert describing the kit and methods/usages for its use. The term "kit" is, for example, also described in WO 2009/141359, which is hereby incorporated by reference.

More specifically, disclosed is a kit, as described above, wherein the binding molecule is selected from the group of monoclonal antibodies or parts thereof, polyclonal antibodies or parts thereof, specific interacting proteins and specific interacting small molecules. The term "binding molecule" is, for example, also described in WO 2009/141359, which is hereby incorporated by reference.

The invention will now be illustrated by the following non-limiting examples.

EXAMPLES

Materials and Methods

Mice

For all experiments, young (12 to 14 weeks), aged (46 to 48 weeks) and old postmenopausal (70 to 72 weeks) female C57BL/6 mice were used (Harlan, Boxmeer, The Netherlands). The mice were bred in a conventional animal facility. Before surgery, mice were kept at least 2 weeks in the animal facility to recover after transport. All experimental procedures were approved by the Ethical Committee of the Faculty of Veterinary Medicine, Ghent University, Belgium.

Uterine Ligation and Inoculation of E. Coli

Mice were anaesthetized with isoflurane (Abbott Laboratories, Kent, United Kingdom) and positioned in right lateral recumbency. The left lateral flank was shaved and disinfected before a 1 cm-long horizontal incision after the costal arch was made. The left uterine horn was ligated cranial to the bifurcatio uteri with a 4-0 polyglactin 910 thread (Vicryl, Ethicon Inc., Gargrave, United Kingdom). The ligated horn was then punctured with a 32-gauge needle and the inoculum (20 µl) was injected. Fluid resuscitation (0.9% NaCl; 0.025 mL/g body weight, consistent with the dosage after CLP (Hubbard et al., 2005) was performed after closure of the abdominal wall (two layers, muscle and skin; 4-0 polyglactin 910). For control purposes, sham operations with inoculation of sterile PBS (Invitrogen, Merelbeke, Belgium) were performed (young-PBS, aged-PBS, old-PBS). Young, aged and old mice were sacrificed 48 hrs p.i. of $10^3$ CFU of E. coli.

An additional group of young mice was inoculated with $10^4$ CFU of E. coli. Forty-eight hours later, they were either euthanized (young-$10^4$) or underwent a partial hysterectomy, i.e., surgical removal of the ligated uterine horn (young-hx).

Surgical Removal of the Ligated Left Uterine Horn

Left horn-hysterectomy was performed in young mice at 48 hrs p.i. of $10^4$ CFU (young-hx). In complete isoflurane anesthesia, sutures of the left abdominal walls were removed. The ligated left uterine horn was localized and ligated at the connection left ovarium—uterine horn top and uterine horn— corpus uteri with 4-0 polyglactin 910. The mesometrium was also ligated before removal of the left horn. Fluid resuscitation and closure of the abdominal wall were performed, as described.

Bacterial Culture

For the intra-uterine inoculation, E. coli strain O18:K1 was used, which was kindly provided by Dr. T. van der Poll. This strain was originally isolated from a clinical case of human sepsis and has been used in various studies of sepsis in mice describing its intraperitoneal inoculation of $10^4$ CFU (Renckens et al., 2006). The number of bacteria recovered from heart, liver, kidneys, spleen and uterus at sacrifice was determined after sterile homogenization and plating onto blood agar. Peritoneal swabs and blood were analyzed for the presence of bacteria.

Clinical Observations

At 48 hrs p.i., mice were classified as alert (rectal body temperature range 37.5-38.5° C., spontaneous motor activity, normal gait), weakened (temperature range 32-36° C., reduced motor activity, abnormal and unsteady gait), lethargic (temperature <30° C., no motor activity, no gait, hunched posture, ruffled coat), or dead.

In Vivo Imaging

Uterine ligation and inoculation was performed with $10^3$ CFU of E. coli Xen14 (BIOWARE™ Microorganism, Caliper Life Sciences), which possesses a stable copy of the Photorhabdus luminescens lux operon on its bacterial chromosome. After anesthesia by inhalation of isoflurane, mice were placed in a light-sealed imaging chamber connected to an ultra-sensitive CCD camera of the IVIS Lumina II imaging device (Caliper Life Sciences, Hopkinton, USA).

Measurement of Cyto- and Chemokines, Serum Creatinine, BUN, and Nitrite

The amount of IL-1β, IL-6, IL-10, TNF, keratinocyte-derived chemokine (KC) and monocyte chemoattractant protein-1 (MCP-1) in plasma was determined according to the protocol of the manufacturer with a murine cytometric bead array flex set on a FACSARRAY™ bioanalyzer system and analyzed using the FCAP Array software (BD Biosciences). The detection limits were 10 pg/ml for IL-1β, IL-6, TNF and KC, and 20 pg/ml for IL-10 and MCP-1. Serum creatinine concentrations were determined with an improved Jaffe method and BUN concentrations with an improved Jung method (QUANTICHROM™ creatinine or urea assay kit, BioAssay Systems, Hayward, USA). Plasma concentrations of nitrite were used to reflect nitric oxide synthesis in vivo and was determined, as described by Cauwels et al. (2010).

Histology of Organs

The 10% formalin-fixed, paraffin-embedded kidney, liver and uterus sections (5 µm) were stained with periodic acid-Schiff reagent and hematoxylin-eosin. Histological changes in the cortex of the kidney and outer medulla were assessed by quantitative measurements of tissue damage (tubular damage score, TDS) at 400× magnification using 10 randomly selected fields for each animal by the following criteria: 0, areas of damage ≤5% of tubules; 1, damage involving 6% to 10% of tubules; 2, damage involving 11% to 25% of tubules; 3, damage involving 26% to 45% of tubules; 4, damage involving 46% to 75% of tubules; 5, >76% of the area being affected (Faubel et al.). Histological criteria for renal damage were tubular epithelial swelling, loss of brush border, vacuolar degeneration, necrotic tubules, cast formation and desquamation. Liver injury was defined as vacuolar degeneration, pleomorphism of hepatocyte nuclei, apoptosis and necrosis, and hepatocellular dissociation. Uterus sections were examined to confirm integrity of the uterine wall.

Western Blot Analysis of Caspase-1, -3 and -7 in Kidney Lysates

For the detection of proteolytic activation of caspase-1, -3 and -7, kidneys were homogenized directly into lysis buffer supplemented with protease inhibitors. Membranes were blocked and incubated with a primary antibody against caspase-1 (Centre d'Economie Rurale, Marloi, Belgium), cleaved caspase-3 and cleaved caspase-7 (Cell Signaling Technology, Danvers, USA). The anti-β-actin antibody was purchased from BD TRANSDUCTION LABORATORIES™ (BD Biosciences).

Analysis of Human Urine Samples

To verify the clinical potential of urinary CHI3L1 and CHIA for diagnosis of AKI or septic AKI, we also collected human urine samples from 12 septic patients, with and without AKI, and from 2 healthy volunteers. Samples were collected at the intensive care unit of Ghent University Hospital under Ethical approval of the Institutional Review Board. Sepsis was defined and classified in accordance with the American college of Chest Physicians and the Society of Critical Care Medicine consensus (Levy et al., 2003). Patients were diagnosed with AKI when ≥1.5 fold increase in sCr from admission or known baseline values was present, in agreement with the AKIN criteria (Mehta et al., 2007).

TUNEL Assay

Immunohistochemical detection and quantification of apoptosis was done on paraffin-embedded kidney sections stained with terminal deoxynucleotidyl transferase (TdT)-mediated nick end labeling (TUNEL) as per the manufacturer's instructions (In situ cell death detection kit, alkaline phosphatase, Roche Diagnostics).

Statistical Analysis

All data were analyzed using the SPSS software (SPSS Inc., Chicago, Ill., USA) at a global significance level of 0.05. Results were expressed as mean±SEM. Comparisons of data at 48 hrs p.i. between the PBS-group and infected group of each age were made using the non-parametric Mann-Whitney U test. Comparisons between PBS-groups of different age and infected mice of different age were made pair wise using the Kruskall Wallis test, with Dunnet or Bonferroni-adjusted comparison-wise significance level of 0.017 (=0.05/3 for PBS groups; =0.05/3 for young, aged and old mice inoculated with $10^3$ CFU; =0.05/3 for young mice infected with $10^3$ or young-$10^4$ at 48 hrs p.i. and young-hx mice at day 7 p.i.). Correlations were conducted according to Spearman. For survival analysis, a Kaplan-Meier analysis followed by a log-rank test was performed.

Supplementary Materials and Methods

Bacterial Culture

Bacteria were grown overnight at 37° C. in Brain Heart Infusion medium. To verify their purity, bacteria were streaked onto a blood agar plate. Bacterial concentration was determined using a standard curve plotting CFU as a function of the absorbance at 550 nm. Sterile PBS was applied to further dilute the culture until the desired concentration of $5\times10^4$ CFU/ml (young, aged, old) or $5\times10^5$ CFU/ml (young-$10^4$). The actual number of CFU injected was confirmed by spreading the inoculum onto an agar plate and counting the colonies after overnight incubation.

Blood was collected by sterile cardiac puncture and heart, liver, kidneys, spleen and uterus were harvested under sterile conditions. Organs were homogenized in 1 ml of sterile PBS. The number of bacteria recovered from organs at 48 hrs p.i. was determined similarly after preparing serial dilutions of organ lysates. Peritoneal swab and blood was analyzed for the presence of bacteria by plating onto blood agar and colony counting after 12 hrs incubation at 37° C.

Clinical Observations

Following intra-uterine inoculation, mice were examined for generalized reactions, such as awareness of the environment, activity and grooming, weakness and mortality. Rectal body temperature was measured every 4 hrs (model C20 type K; Comark Electronics), as well as food and water uptake and body weight.

In Vivo Imaging

Gray scale images were obtained before luminescence imaging to localize the ligated uterine horn, which was detectable by visualization of both left flank and left ventral half of the abdomen. Luminescence of the mice was recorded at 5 cm field of view, bin=16 and an exposure time of 120 seconds. Excised organs were imaged in a similar way, with settings adapted to individual organs' detectable radiance (p/s/sr/cm$^2$). Images were analyzed with the Living Image software (Caliper Life Sciences).

Measurement of Nitrite in Plasma

Plasma concentrations of nitrite were used to reflect NO synthesis in vivo and was determined, as described by Cauwels et al. (2010). Briefly, for nitrite determination, serum was diluted 1:1 with $5.10^9$ CFU/ml *Pseudomonas oleovorans* suspension (reducing nitrate to nitrite) and incubated at 37° C. for 3-4 hrs. After centrifugation, the supernatant was diluted 1:2 with Griess reagent, and proteins were precipitated with 10% TCA. The absorbance of the supernatant was measured at 540 nm. Total nitrite was calculated from a standard curve.

Western Blot Analysis of Caspase-1, -3 and -7 in Kidney Lysates

For the detection of proteolytic activation of caspase-1, -3 and -7, one half of the left and right kidney was homogenized directly into lysis buffer (10 mM Tris HCl pH7.4, 200 mM sodium chloride, 5 mM EDTA, 1 mM oxidized glutathione, 10% glycerol and 1% NP-40) supplemented with protease inhibitors (0.15 µM aprotinin, 2.1 µM leupeptin and 100 nM phenylmethylsulfonyl fluoride; Sigma-Aldrich). The remaining lysate was centrifuged at 5000 g at 4° C. for 30 min. Laemmli buffer (final concentration of 62.5 mM Tris HCl pH 6.8, 100 mM β-mercaptoethanol, 2% sodium dodecyl sulphate, 0.1% bromophenol blue and 10% glycerol) was added to the supernatant after determination of the protein concentration using the Bradford method (BIO-RAD® protein assay, Bio-Rad Life Science, Nazareth, Belgium). Samples were boiled for 15 min and loaded onto a polyacrylamide gel (15%). Following electrophoresis, proteins were transferred to a nitrocellulose membrane by semi-dry blotting. Membranes were blocked and then incubated with a primary antibody. Secondary antibodies conjugated to horseradish peroxidase were applied and immunoreactive proteins were visualized using chemiluminescence substrate (Perkin Elmer, Massachusetts, USA) on blots exposed to a film (Amersham Biosciences, Roosendaal, The Netherlands).

Gel-Free Proteomics of Urine of Mice Before and after Septic Insult

Urine Collection

Mice were individually housed in metabolic cages (Tecniplast, Buguggiate, Italy) and urine was collected overnight, both before (−15 hrs to −3 hrs; $T_0$) and after (36-48 hrs; $T_1$) uterine ligation and inoculation. Urine was collected with protease inhibitors (COMPLETE®, Mini, EDTA-free, Roche Diagnostics, Mannheim, Germany) in a 1:7 ratio of buffer to urine and consecutively centrifuged at 300 g at 4° C. for 5 minutes (min). The supernatant was subjected to an additional centrifugation at 2000 g for 10 min, then aliquoted and immediately frozen at −80° C. No more than 2 freeze-thaw cycles were allowed for each aliquot.

Study Population for Urinary Gel Free Proteomics

We investigated changes in the urinary proteome that could represent potential biomarkers or elucidate important mechanisms in sepsis-induced AKI by comparing urine from septic mice (S) with urine from septic mice with AKI (S+AKI). Separate pools of urine collected from S (n=7) and S+AKI (n=5) mice were prepared. The urine of S and of S+AKI mice was respectively pooled based on equal amounts of urinary protein from each individual mouse within its group. Comparative proteome analysis of pooled urine before ($T_0$) and after ($T_1$) inoculation was done within each group, as well as between the two different groups ($T_1$ versus $T_1$; $T_0$ versus $T_0$).

Discovery of Candidate Urinary Biomarkers by Gel-Free Proteome Analysis

Endoproteinase Lys C Digestion and Postmetabolic Labeling of Urinary Samples

Approximately 150 µg of proteins were used from each sample (S+AKI $T_0$ and $T_1$, and S $T_0$ and $T_1$), the volume was adjusted to 1 mL using 100 mM of Tris pH 8.7 (150 µg was approximately equal to a volume of 750 µL, hence 250 µL of the 100 mM Tris pH 8.7 was added). Alkylation of cysteines was carried out using 20 mM iodoacetamide (IA, Sigma-Aldrich, Steinheim, Germany) and 5 mM of (tris(2-carboxyethyl)phosphine) (TCEP, ThermoScientific, Waltham, Mass., USA) for 30 min at 37° C. Following alkylation, excess reagents were removed on a NAP™-10 desalting column (Amersham Biosciences, Uppsala, Sweden) and proteins were collected in L5 mL of 50 mM tricarboxyethyl ammonium bicarbonate (TEAR, Sigma-Aldrich).

Prior to digestion, protein concentrations were measured again by the Bradford assay. Proteins were denatured at 95° C. for 10 min followed by cooling-down on ice for 15 min. To each sample 2.5 μg of endoproteinase Lys C (endoLys C, Roche Diagnostics Gmbh, Mannheim, Germany) was added and digestion was carried out overnight at 37° C.

Labeling of peptides was performed by propionylation, as described in Ghesquière et al, 2009. Briefly, peptides from S+AKI $T_0$ and from S $T_1$ were labeled with light isotopic variant ($^{12}C3$) of NHS-propionyl and the peptides from S+AKI $T_1$ and S $T_0$ were modified with the heavy isotopic variant ($^{13}C3$) of the NHS-propionyl ester. Practically, we added 2 mg of the NHS-propionyl ester to 100 μg of digested proteins, the reaction lasted 150 min at 37° C. Excess reagent was removed by adding 60 μL of a 1M stock glycine to the sample for 15 min at 25° C. Removal of unwanted O-propionylation was done by adding 20 μL of hydroxylamine (Sigma-Aldrich) for 15 min at 25° C. Samples were then acidified to 1% TFA f.c. (trifluoroacetic acid, Sigma-Aldrich). Finally, 50 μg of each labeled sample was mixed, according to the following scheme:

| $^{12}C$ sample | $^{13}C$ sample |
|---|---|
| S + AKI $T_0$ | S + AKI $T_1$ |
| S $T_1$ | S $T_0$ |
| S $T_1$ | S + AKI $T_1$ |
| S + AKI $T_0$ | S $T_0$ |

All of the mixtures were vacuum dried, re-dissolved in 100 μL of solvent A and separated onto a RP-HPLC column (2.1 mm internal diameter×150 mm (length) 300SB-C18, ZORBAX®, Agilent, Waldbronn, Germany) using an Agilent 1100 Series HPLC system. Following a 10 min wash with HPLC solvent A (0.1% TFA in water/acetonitrile, 98/2 (v/v), water (LC-MS grade, Biosolve, Valkenswaard, The Netherlands) and acetonitrile (HPLC grade, Baker, Deventer, The Netherlands)), a linear gradient to 100% solvent B (0.1% TFA in water/acetonitrile, 30/70 (v/v)) was applied over 100 min. Using Agilent's electronic flow controller, a constant flow of 80 μL/min was used.

Peptides that eluted between 20 and 80 min were collected into 60 fractions (1 min each, containing approximately 80 μl) and fractions that were separated by 15 min were put together, reducing the number of samples for a differential analysis to 15. These were then vacuum dried and re-dissolved in 50 μL 2.5% acetonitrile.

LTQ-OrbiTRAP® Analysis

We analyzed the obtained fractions onto an Ultimate 3000 nano-HPLC system in-line connected to a LTQ OrbiTRAP® XL mass spectrometer. 2.5 μL of each sample was used for LC-MS/MS analysis using an Ultimate 3000 HPLC system (Dionex, Amsterdam, The Netherlands) in line connected to an LTQ OrbiTRAP® XL mass spectrometer (Thermo Electron). Each sample was measured three times (technical replicates). Peptides were first trapped on a trapping column (PEPMAP™ C18 column, 0.3-mm inner diameter×5 mm (Dionex)), and following back-flushing from the trapping column, the sample was loaded on a 75-μm-inner diameter×150-mm reverse-phase column (PEPMAP™ C18, Dionex). Peptides were eluted with a linear gradient of a 1.8% solvent B' (0.05% formic acid in water/acetonitrile (2:8, v/v)) increase per minute at a constant flow rate of 300 nL/min. The mass spectrometer was operated in data-dependent mode, automatically switching between MS and MS/MS acquisition for the six most abundant ion peaks per MS spectrum. Full-scan MS spectra were acquired at a target value of 1e6 with a resolution of 30,000. The six most intense ions were then isolated for fragmentation in the linear ion trap. In the LTQ OrbiTRAP®, MS/MS scans were recorded in profile mode at a target value of 5,000. Peptides were fragmented after filling the ion trap with a maximum ion time of 10 ms and a maximum of 1e4 ion counts. From the MS/MS data in each LC-run, Mascot generic files (mg) were created using the Mascot Distiller software (version 2.2.1.0, Matrix Science Ltd.). When generating these peak lists, grouping of spectra was performed with a maximum intermediate retention time of 30 s and maximum intermediate scan count of 5 used where possible. Grouping was done with 0.1-Da tolerance on the precursor ion. A peak list was only generated when the MS/MS spectrum contained more than 10 peaks, no de-isotoping was performed, and the relative signal to noise limit was set at 2. Such generated peak lists were then searched with Mascot using the Mascot Daemon interface (version 2.2.0, Matrix Science Ltd.).

Spectra were searched against the Swiss-Prot database (version 56.4) and taxonomy was set to *Mus musculus* (15,988 entries). Enzyme was set to Endoproteinase LysC. Variable modifications were set to pyro-glutamate formation of N-terminal glutamine and acetylation of the protein's N-terminus and methionine oxidation. Carbamidomethylated cysteines were set as a fixed modifications. Mass tolerance of the precursor ions was set to ±10 ppm and of fragment ions to ±0.5 Da. The peptide charge was set to 1+, 2+ or 3+ and one missed cleavage site was allowed. Also, Mascot's C13 setting was to 1, and note that now $^{12}C3$- or $^{13}C3$-N-propionylation were selected as the isotope labels (exclusive modifications) in the Mascot Distiller environment. Only peptides that were ranked one and scored above the identity threshold score set at 99% confidence were withheld.

For the analysis of the differential data we only used those proteins that were identified in all three replicate analyses and validated them using the software tool Rover (Colaert et al.), which is supported by the MS-LIMS data platform (Helsens et al.). Since protein ratios were based on equal amount of protein loaded on MS and not on equally loaded volumes of urine, correction for variation in urine flow rate (by means of urinary creatinine) was not standard performed. Proteins were considered over- or underexpressed when ratios >2.0 or <0.5 were found, respectively. Correction of ratios for urinary creatinine did not affect marker selection approaches.

Validation of Candidate Urinary Biomarkers for Sepsis-Induced AKI

Western Blot Analysis of Urine, Serum and Renal Tissue Homogenates

For the validation of the discovered candidate biomarkers by western blot analysis of urine, Laemmli buffer was added to the supernatant after determination of the protein concentration using the Bradford method (BIO-RAD® protein assay, Bio-Rad Life Science, Nazareth, Belgium), A similar protocol was performed to prepare plasma samples for western blot analysis. For the detection of their presence in the kidney, one half of the left and right kidney was combined and homogenized directly into lysis buffer (10 mM Tris HCl pH 7.4, 200 mM sodium chloride, 5 mM EDTA, 1 mM oxidized glutathione, 10% glycerol and 1% NP-40) supplemented with protease inhibitors (0.15 μM aprotinin, 2.1 μM leupeptin and 100 nM phenylmethylsulfonyl fluoride; Sigma-Aldrich). The remaining lysate was centrifuged at 2000 g and 4° C. for 30 minutes and Laemmli buffer was also added to the supernatant after determination of the protein concentration. All urine, plasma and kidney lysate samples were boiled for 15 minutes and loaded onto a polyacrylamide gel (12% and 18%). Following electrophoresis, proteins were transferred to a nitrocellulose membrane by semi-dry blotting. Membranes were blocked and then incubated with a primary antibody against mouse NGAL (rabbit polyclonal), osteopontin (OPN, goat polyclonal), cathepsin L1 (CATHL1, rat monoclonal), uteroglobin (UT, rabbit polyclonal), gelsolin (rabbit polyclonal), thioredoxin (TRX, mouse monoclonal), sepiapterin reductase (SPR, C-terminal region), chitinase 3-like protein 3 (CHI3L3, rat monoclonal), chitinase 3-like protein 1 (CHI3L1, goat polyclonal), and acidic mammalian chitinase (CHIA, rabbit polyclonal) and against human NGAL (rabbit polyclonal), CHI3L1 (goat polyclonal) and CELIA (rabbit polyclonal), purchased from Abeam (Cambridge, UK; NGAL, UT, gelsolin, TRX, CHIA), R&D Systems (Oxon, UK; OPN, CATHL1, CHI3L3, CHI3L1) or Abgent (San Diego, USA; SPR). The anti-β-actin antibody was purchased from BD TRANSDUCTION LABORATORIES™ (BD Biosciences). Secondary antibodies conjugated to horseradish peroxidase were applied and immunoreactive proteins were visualized using chemiluminescence substrate (Perkin Elmer, Massachusetts, USA) on blots exposed to a film (Amersham Biosciences, Roosendaal, The Netherlands).

Human Study Population

To verify the clinical potential of urinary NGAL, CHI3L1 and CHIA, we also collected spot human urine samples from ten septic patients, with and without AKI, and from two healthy volunteers. Samples were collected at the Ghent University Hospital under approval of the Institutional Review Board. Patients were diagnosed with AKI when ≥1.5 fold increase in sCr from admission or known baseline values was present, in agreement with the AKIN criteria (Mehta et al., 2007).

Statistical Analysis

All data were analyzed using the SPSS software (SPSS Inc., Chicago, Ill., USA) at a global significance level of 0.05. Results were expressed as mean±standard deviation (SD). Comparisons of data at $T_1$ between aged PBS-inoculated, S and S+AKI mice were made pair wise using the Kruskall Wallis test, with Dunnet or Bonferroni-adjusted comparisonwise post hoc test at a significance level of 0.017 (=0.05/3). Data of $T_0$ and $T_1$ within one group of mice were compared using the Wilcoxon matched pairs test.

Results

Characterization of Uterine Ligation and Inoculation (ULI) of *E. coli* as Model for Sepsis Several criteria for a clinically relevant sepsis model have been described (Hubbard et al., 2005; Kubiak et al., 2010; Dyson et al., 2009; Deitch, 1998). In agreement with the definition and staging of sepsis (Levy et al., 2001), a mouse model for sepsis should (i) show clinical observations consistent with sepsis and septic shock, which precede mortality (ii-iv) generate bacteremia and systemic infection resulting from the infectious focus, with bacterial proliferation in distant organs, (v) have an initial hyperinflammatory state followed by a hypoinflammatory and hypotensive host response.

(i) Optimalisation of the Model and Clinical Observations after ULI

Figure 9:
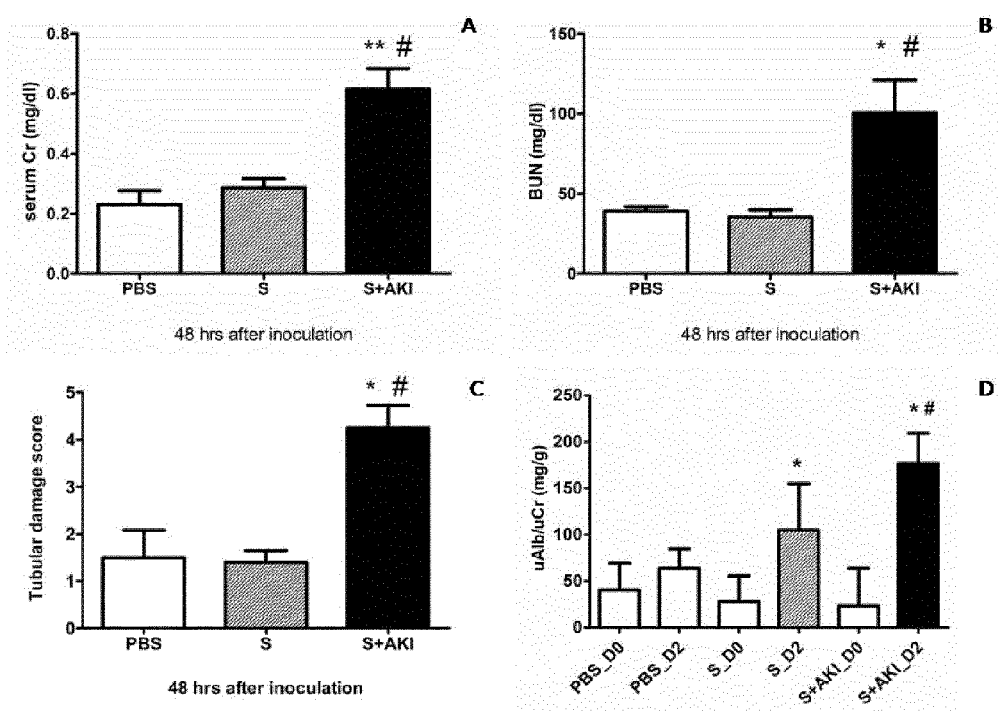
FIG. 9: Serum creatinine (sCr), blood urea nitrogen (BUN) concentrations, urinary albumin to creatinine ratios and renal histological changes in septic mice. Concentrations of sCr (A) and BUN (B), and tubular damage score (C) at 48 hours after inoculation (p.i.) of $10^3$ CFU of *E. coli* or PBS in aged mice. Accordingly, mice were classified as septic without acute kidney injury (S) or septic with acute kidney injury (S+AKI). Urinary albumin to creatinine ratios before ($T_0$) and 48 hours after ($T_1$) inoculation with *E. coli* or PBS (D). Representative renal histological damage at 48 hours p.i. with PBS (E) or *E. coli* of mice without AKI (F) and with AKI (G). Kidney sections are stained with hematoxylin-eosin, original magnification, ×400. Combined results of independent experiments are shown (n=5-7 mice per group). Data are means±SD. *, $p<0.05$ and **, $p<0.01$ compared to age-matched PBS controls; #, $p<0.05$ compared to S mice.
Figure 9:
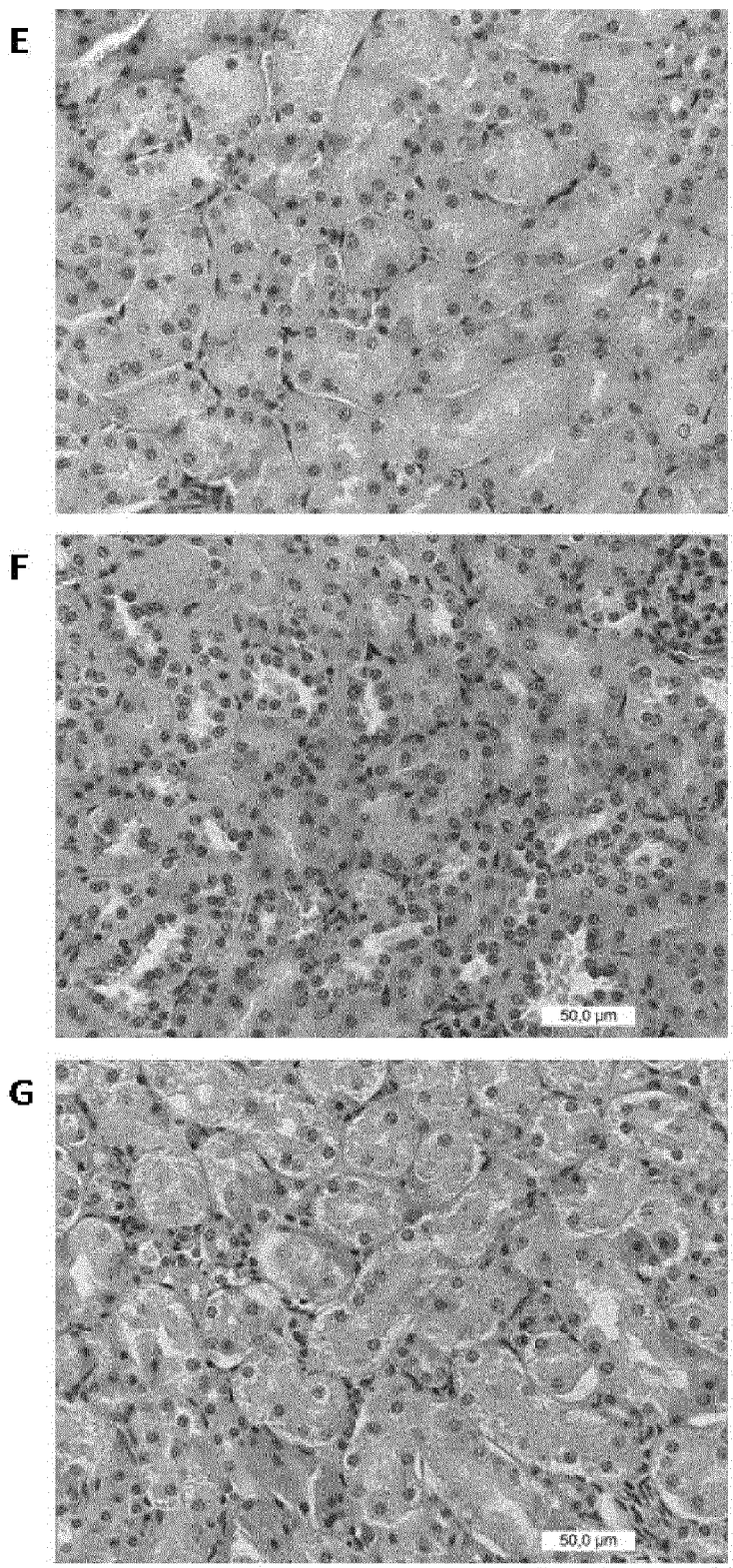
Figure 10:
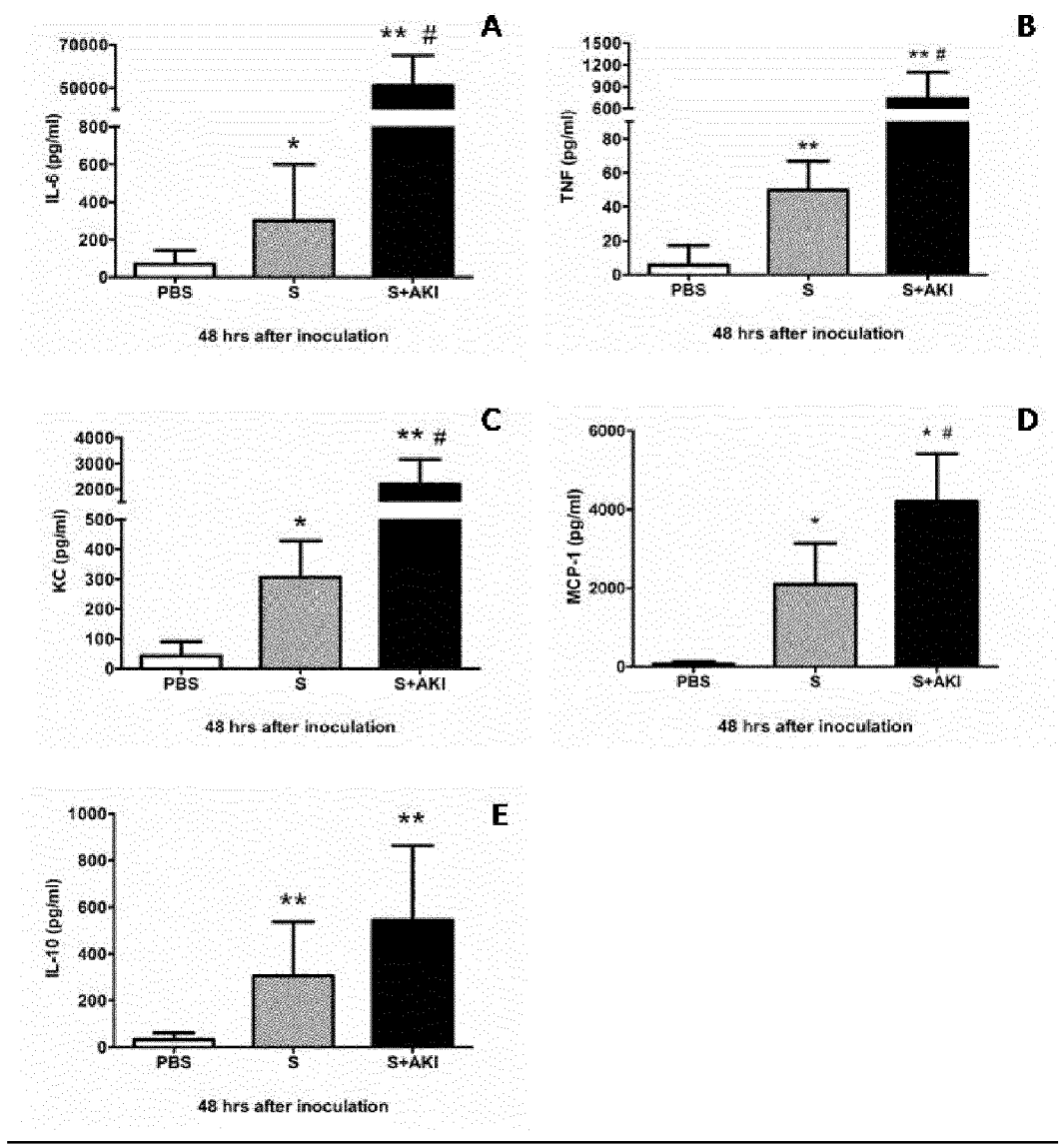
FIG. 10: Plasma cyto- and chemokine profiles of septic mice. Plasma concentrations of IL-6 (A), TNF (B), KC(C), MCP-1 (D), and IL-10 (E) were measured 48 hours after inoculation (p.i.) with $10^3$ CFU of *E. coli* or PBS in aged mice. Septic mice were classified as septic without acute kidney injury (S) or septic with acute kidney injury (S+AKI). The combined results of independent experiments are shown (n=5-7 mice for each group). Data are means±SD. *, $p<0.05$ and **, $p<0.01$ compared to age-matched PBS control mice; #, $p<0.05$ compared to S mice.

Based on preliminary experiments (not shown), both the inoculum dose and endpoint was set at $10^3$ colony forming units (CFU) of *E. coli* and 48 hours (hrs) after inoculation (p.i.), respectively. This combination allows the comparison between the three age categories (young, aged, old). Higher inoculum dose or later endpoints resulted in earlier death or higher mortality rates of aged and old mice. Inoculation of young mice with $10^4$ CFU (young-$10^4$) resulted in a higher proportion of severe septic or septic shock animals compared to inoculation with $10^3$ CFU. Mortality at 48 hrs increased with age (FIG. 1). Clinical classification as alert, weakened or lethargic included normothermia, moderate hypothermia or severe hypothermia, respectively. The animals that died or were classified as lethargic showed typical signs of septic shock (Barrera et al., 2010), with post-mortem diagnosis of kidney and liver injury (FIG. 9). Clinical observations consistent with more severe illness were found with increasing age (weakened-lethargic: young, 17-8%; young-$10^4$, 25-17%; aged, 8-31%; old, 14-36%). Phosphate buffered salin (PBS)-inoculated mice (sham) were alert during the experiments.

Figure 2:
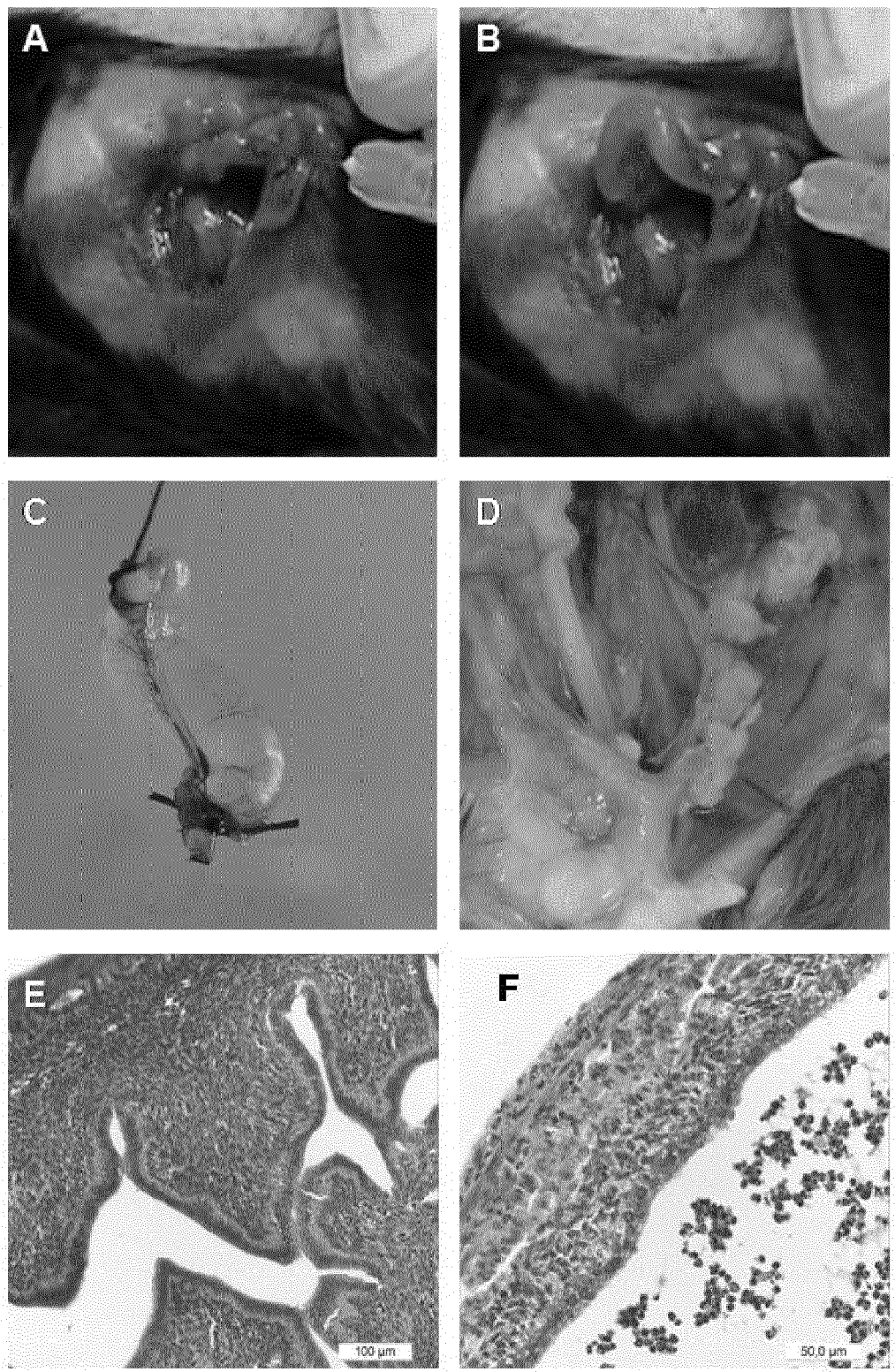
FIG. 2: Technique of uterine ligation and inoculation of bacteria in mice and removal of infected uterine horn. (A) Ligation and (B) inoculation of the uterus with 20 μl of inoculum. (C) Removed left ligated uterine horn and (D) abdominal situs 5 days after removal of the infected left uterine horn. Histology of uterus 48 hours after inoculation of phosphate-buffered saline (E) or *E. coli* (F) with presence of infiltrating neutrophils in the lumen (F). Uterus sections were stained with hematoxylin-eosin. Original magnification, ×200 (E), ×400 (F).
Figure 3A:
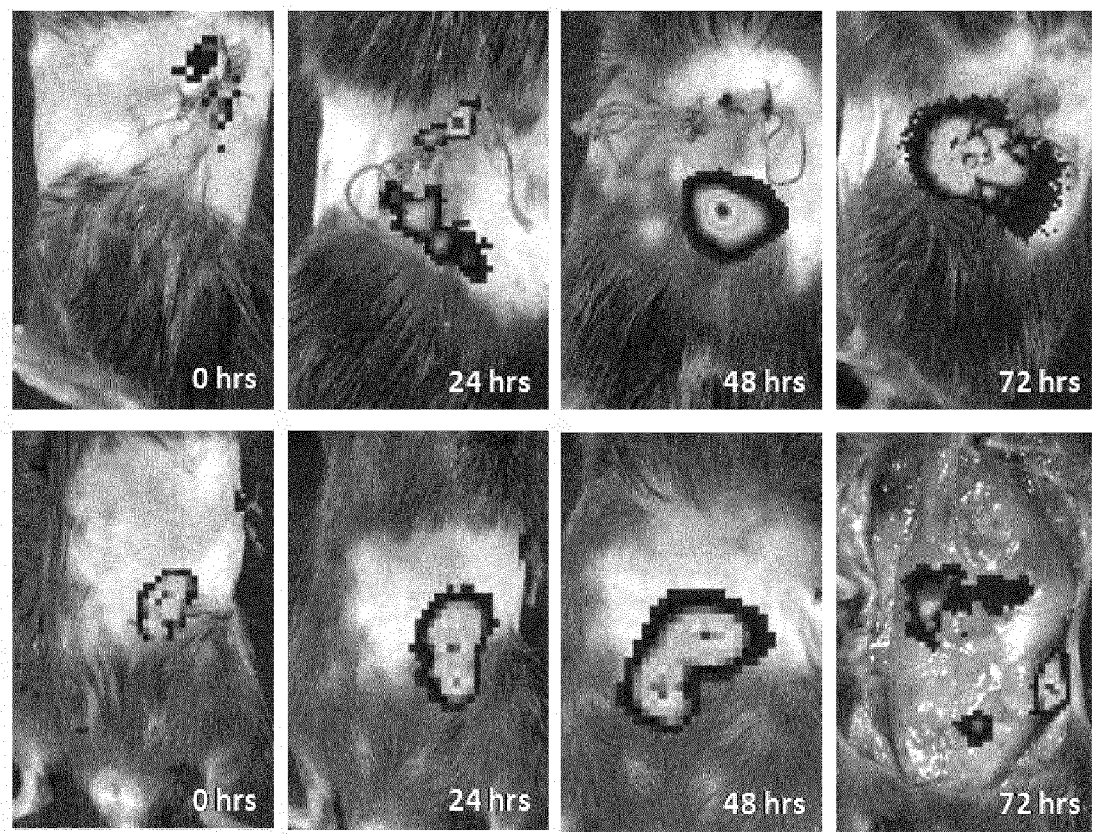
FIG. 3: In vivo imaging of C57BL/6 mice after uterine ligation and inoculation of $10^3$ CFU of bioluminescent *E. coli* or PBS. (A) Upper and lower rows show representative lateral and ventral view images, respectively, at inoculation (0 hours), 24 hours, 48 hours and 72 hours, including corresponding luminescent values (p/s/cm²/sr) (B) Representation of (A) in graphs. (C) Shows the luminescent signal at 72 hours after inoculation with *E. coli* Xen14 of the excised uterus (A), spleen (B), heart (C), lung (D), liver (E) and kidneys (F), respectively.
Figure 3B:
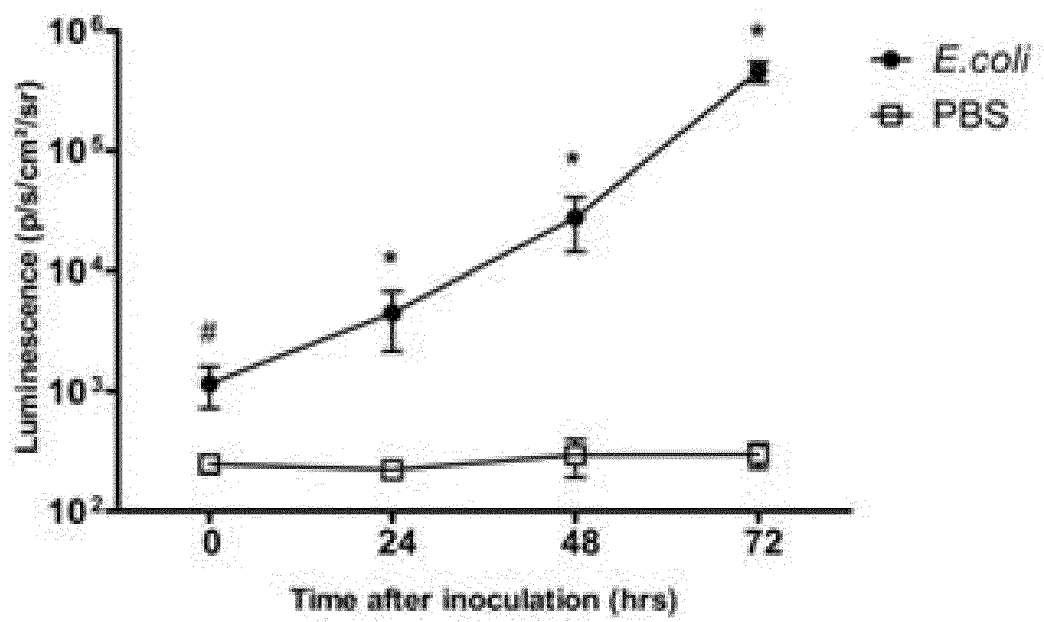
Figure 3B:
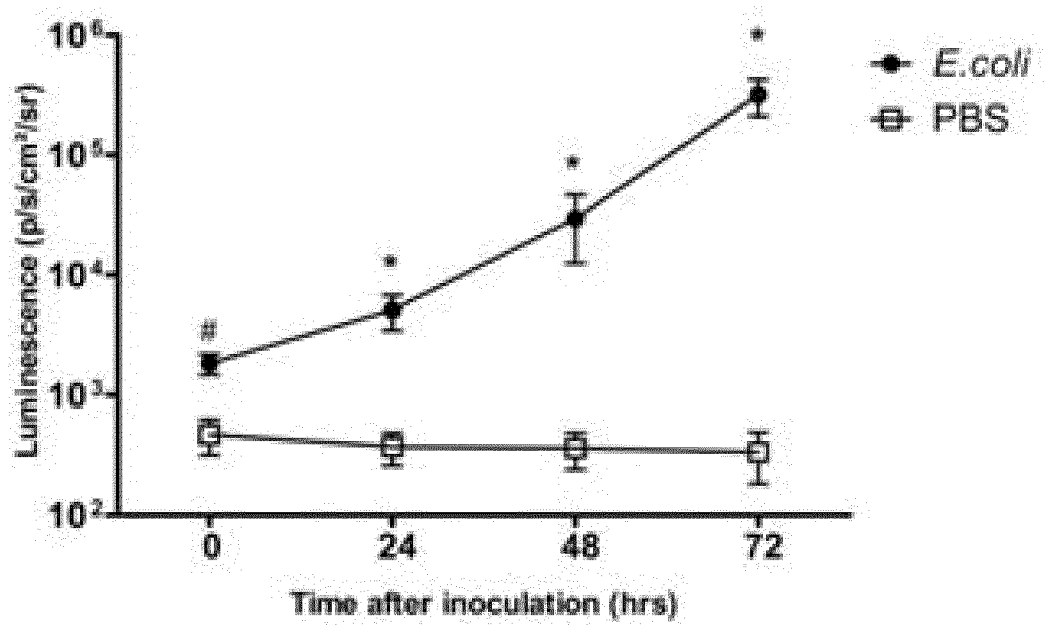
Figure 3C:
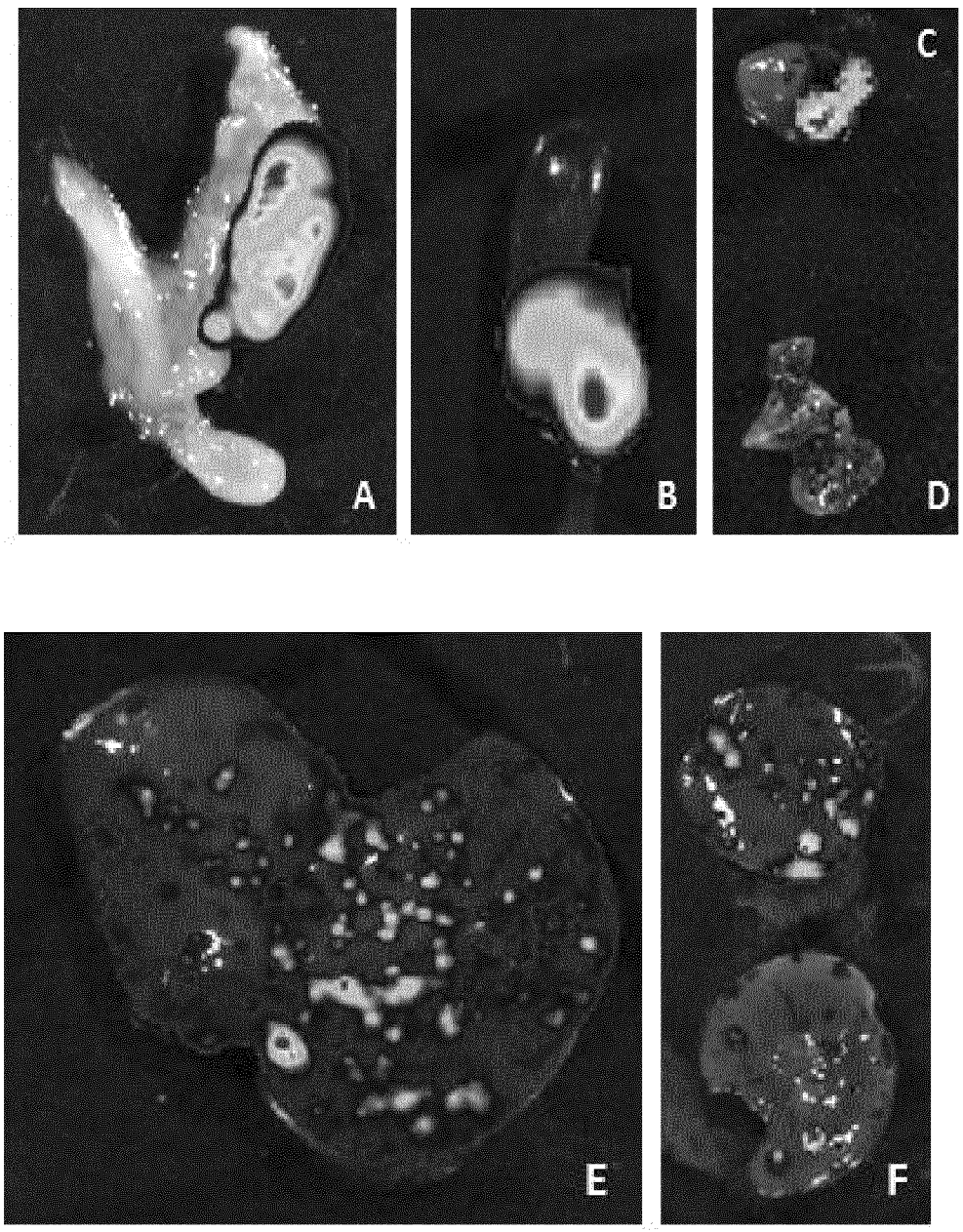
Figure 8:
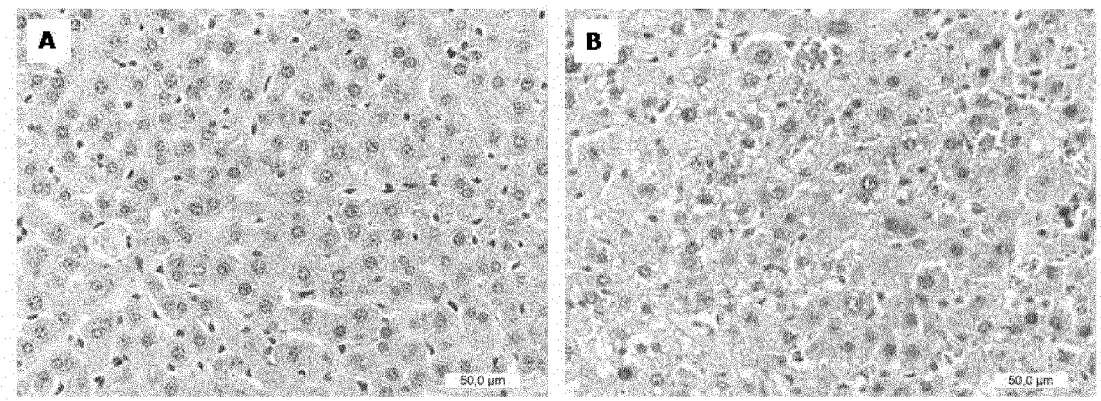
FIG. 8: Liver injury in mice with severe sepsis. Representative liver histological damage is shown 48 hours after inoculation (p.i.) with PBS (A) or *E. coli* (B). Liver sections are stained with hematoxylin-eosin, original magnification, ×400. The liver damage was defined as vacuolar degeneration, pleomorphism of hepatocyte nuclei, apoptosis and necrosis, and hepatocellular dissociation.

(ii) Bacteremia and Replication of *E. Coli* in Distant Organs after Inoculation Bacteremia was detected as early as 24 hrs after infection and was present in all infected mice at 48 hrs p.i. High counts of *E. coli* were present at 48 hrs in heart, liver, spleen and kidneys of infected mice, as well as in blood (FIG. 8). Body temperature was inversely correlated with the bacterial load of distant organs (CFU/g organ) (r=−0.78, p<0.01). Bacterial counts of the ligated uterine horn were not statistically significant between the three different age categories ($2.0×10^9±1.8×10^8$ CFU/g). PBS-inoculated mice had no detectable bacterial counts in organs, blood or peritoneum. An intact uterine wall was found on histological examination, with compression of all layers compared to PBS-inoculated mice and presence of neutrophils in the uterine lumen (FIG. 2). Negative bacterial culture results were obtained from the peritoneal cavity at inoculation and at 24 hrs. At 48 hrs, the minority of mice had positive peritoneal culture results. Only swabs taken in the close proximity of the uterus were positive, which is indicative for a mild and focal peritonitis. The presence of peritonitis was not correlated with severity of clinical observations nor with hypothermia.

All young-$10^4$ mice died within 7 days after infection at the latest. Removal of the left uterine horn (young-hx) resulted in survival of 93% of young mice at day 7 (FIG. 1). At this time, all surviving young-hx mice were alert. Bacterial counts of heart, liver, spleen and kidneys were significantly lower at day 7 p.i. than in young-$10^4$ mice at 48 hrs p.i (FIG. 8). Moreover, bacteria were not present anymore in blood.

(iii) In Vivo Imaging Visualizes the Focus of Infection and Dynamics of the Model Immediately after inoculation (0 hrs), lateral and ventral luminescence values of mice inoculated with bioluminescent *E. coli* Xen14 ($1.1×10^3±0.2×10^3$ p/s/cm²/sr) were comparable to the inoculated dose ($1.1×10^3±0.1×10^3$ CFU). Luminescence was further measured each 12 hrs until 72 hrs p.i., and a tenfold increase was observed per 24 hrs (FIG. 3). Starting from 60 hrs, when mice became clinically depressed, luminescent signal was also detectable in other organs than the uterus. At this time, the highest values were measured in the liver, followed by the kidneys and spleen. No signal was detected in the opened peritoneal cavity, nor in the urine bladder, the right uterine horn, and in PBS-inoculated controls. After overnight incubation, plated organ lysates of *E. coli* Xen14-infected mice showed luminescence, proving that the inoculated bacteria replicated and spread to the organs after infection.

(Iv) Cyto-, Chemokine and Nitrite Response to Sepsis

Figure 4:
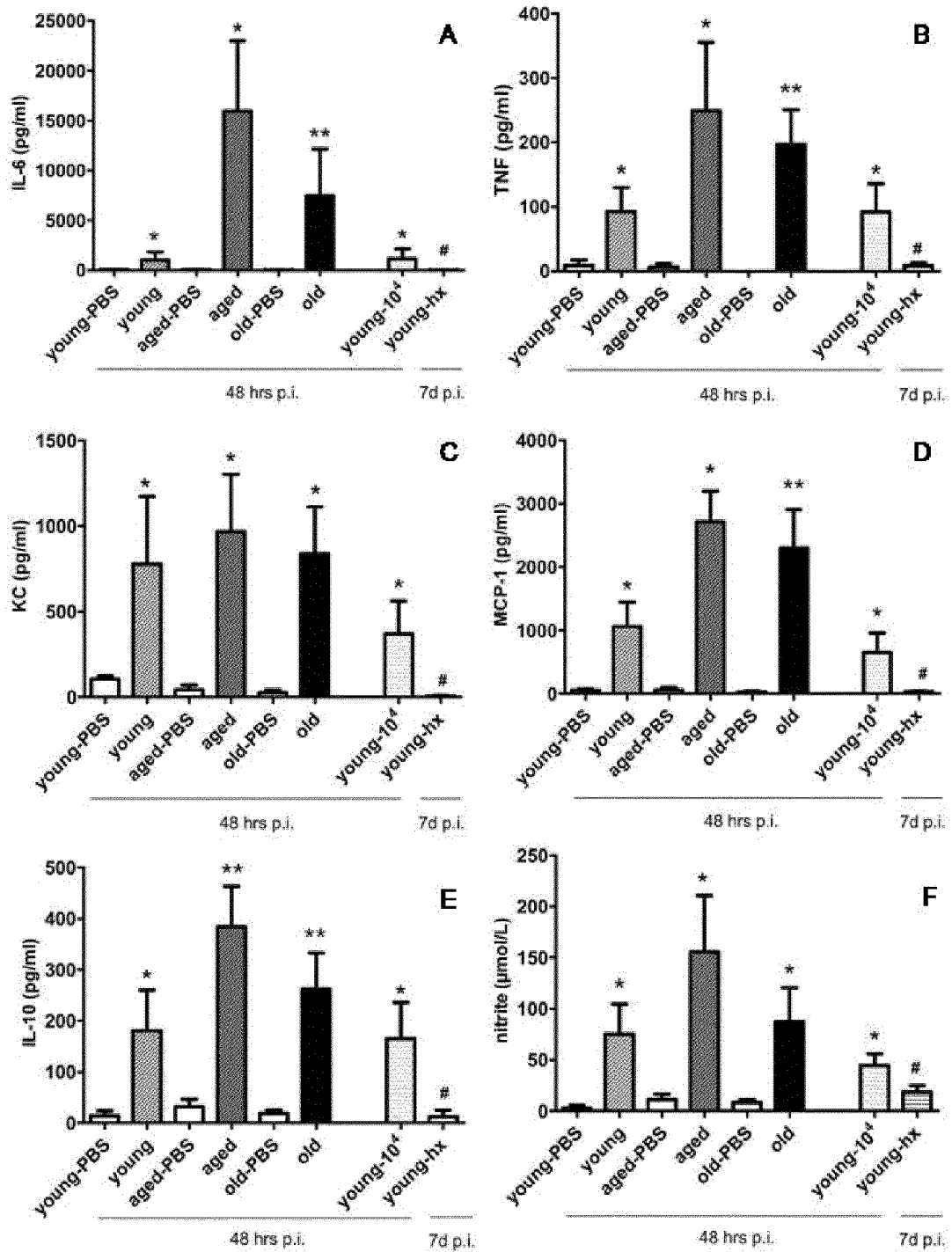
FIG. 4: Plasma cyto- and chemokine profiles, and nitrite concentrations. Plasma concentrations of IL-6 (A), TNF (B), KC(C), MCP-1 (D), IL-10 (E) and nitrite (F) were measured 48 hours after inoculation (p.i.) with $10^3$ CFU of *E. coli* or PBS in young, aged and old mice, or with $10^4$ CFU in young mice (young-$10^4$), and at 7 days (d) p.i. with $10^4$ CFU in young mice which underwent removal of the inoculated uterus at 48 hours (young-hx). The combined results of independent experiments are shown (n=15 for each group inoculated with *E. coli*, and n=5-7 for mice inoculated with PBS). Data are means±SEM. *, $p<0.05$ and **, $p<0.01$ compared to age-matched PBS control mice; #, $p<0.05$ compared to young-$10^4$ mice.

Plasma IL-β levels at 48 hrs were below the detection limit in all mice. Plasma concentrations of IL-6, TNF, KC, MCP-1 and IL-10 were significantly increased at 48 hrs p.i. in infected compared to PBS-inoculated mice (FIG. 4). An increase in cyto- and chemokine concentrations was already observed at 24 hrs. Plasma IL-6, TNF, IL-10 and MCP-1 concentrations were significantly higher in aged and old infected mice than in young infected animals (p<0.05), and were correlated with bacterial load of organs (CFU/g) and with temperature (r=0.68-0.87, p<0.01 and r=−0.69-0.91, p<0.01), with old mice showing the highest correlation degree. Increased plasma concentrations of nitrite were detected at 48 hrs p.i. of *E. coli*, indicating a possible hypotension. Removal of the infected ligated uterine horn resulted in significantly decreased plasma cyto- and chemokine and nitrite concentrations at day 7 p.i. compared to concentrations at 48 hrs p.i. in young-$10^4$ mice. These concentrations in young-hx mice were not statistically different from levels of young PBS-controls at 48 hrs p.i.

B) Renal Response after *E. Coli* Sepsis and Involvement of Caspases (i) Sepsis-Induced AKI is Detected at 48 Hrs after ULI of *E. Coli*

Figure 6:
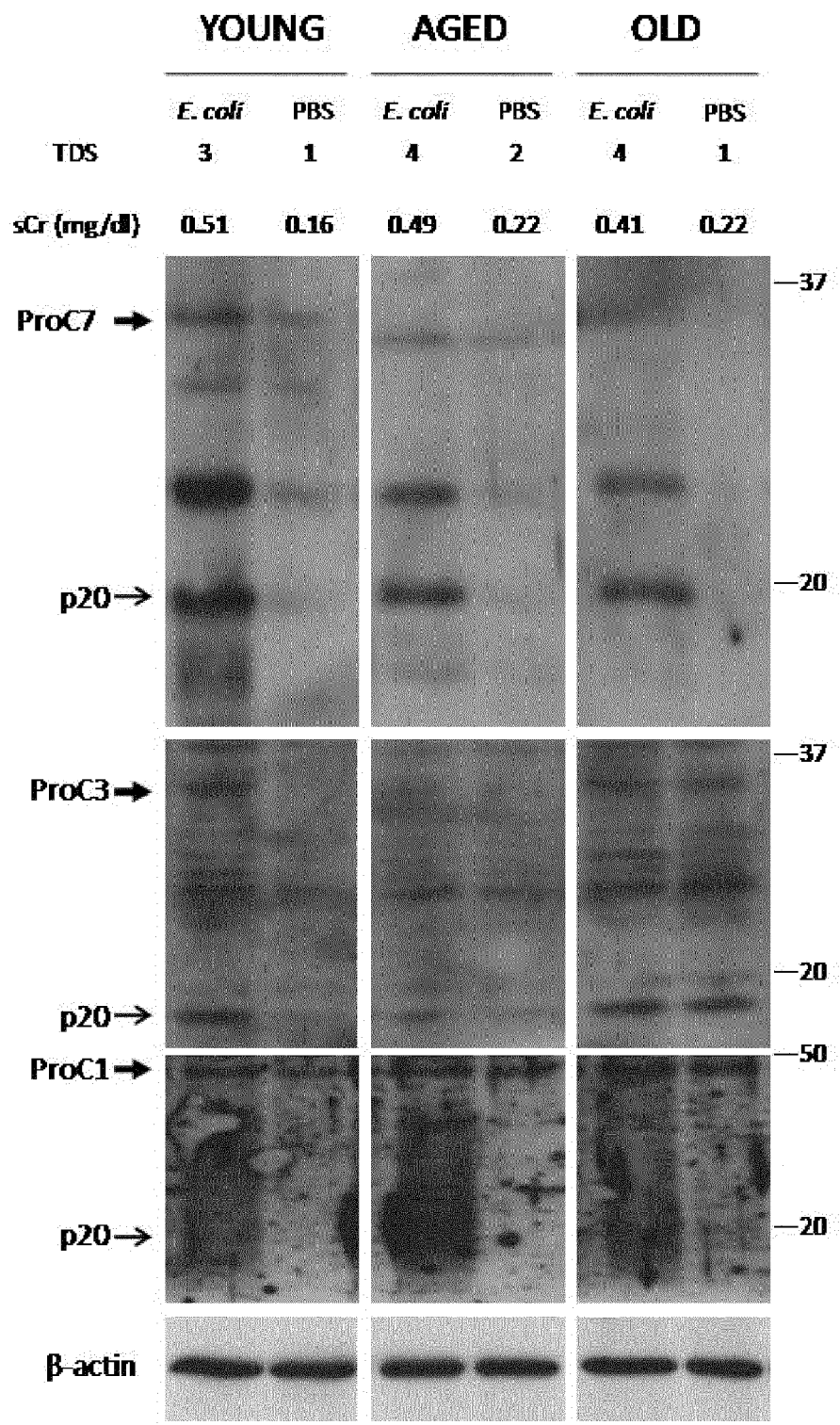
FIG. 6: A. Western blot analysis of caspase-1, -3 and -7 in kidney lysates at 48 hours after inoculation (p.i.) of *E. coli* or PBS in young, aged and old mice. Serum creatinine concentrations (sCr) and tubular damage score (TDS) are presented. Only young and aged mice with AKI (AKIN 2) or ARF (AKIN 3), or with a TDS>2 at 48 hours p.i. of *E. coli* showed activation of caspases (open arrows). Old mice have caspase-3 activation at 48 hours p.i. of PBS and *E. coli*, and activation of caspase-1 and -7 at 48 hours p.i. of *E. coli*. β-actin protein levels served as a loading control. All samples were analyzed at least three times (n=8 per group).
Figure 6:
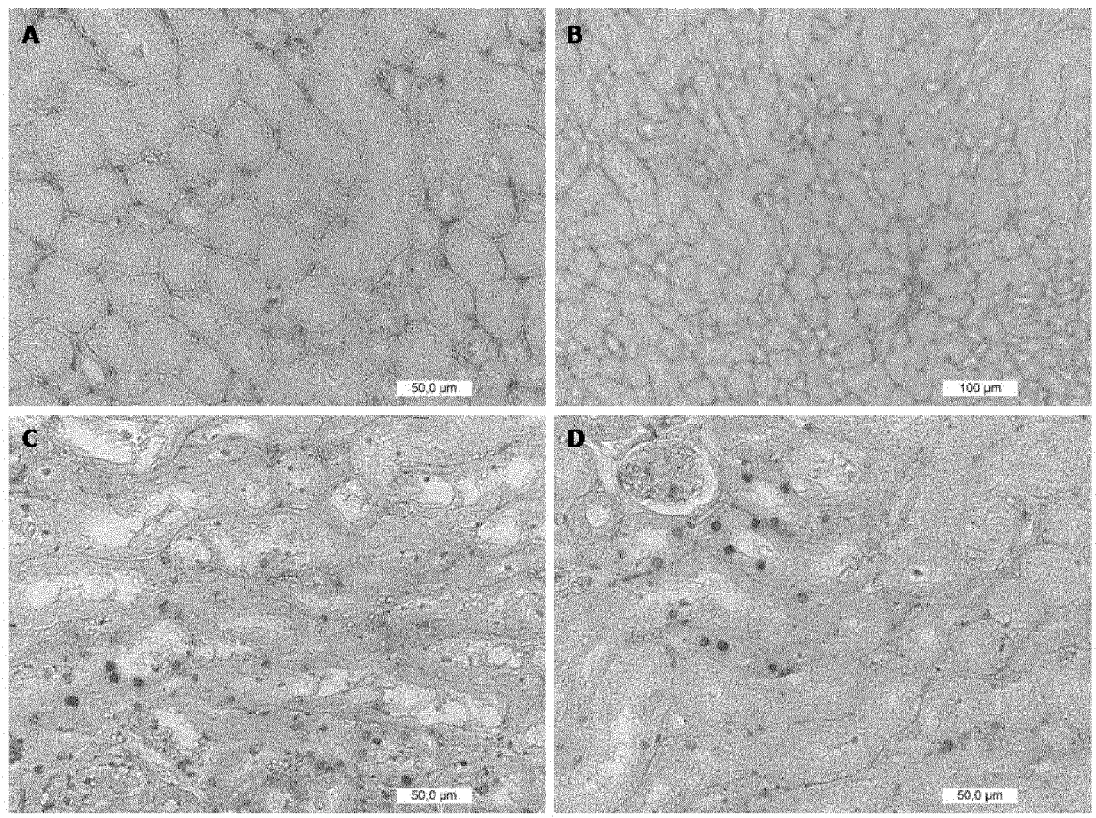
Figure 7:
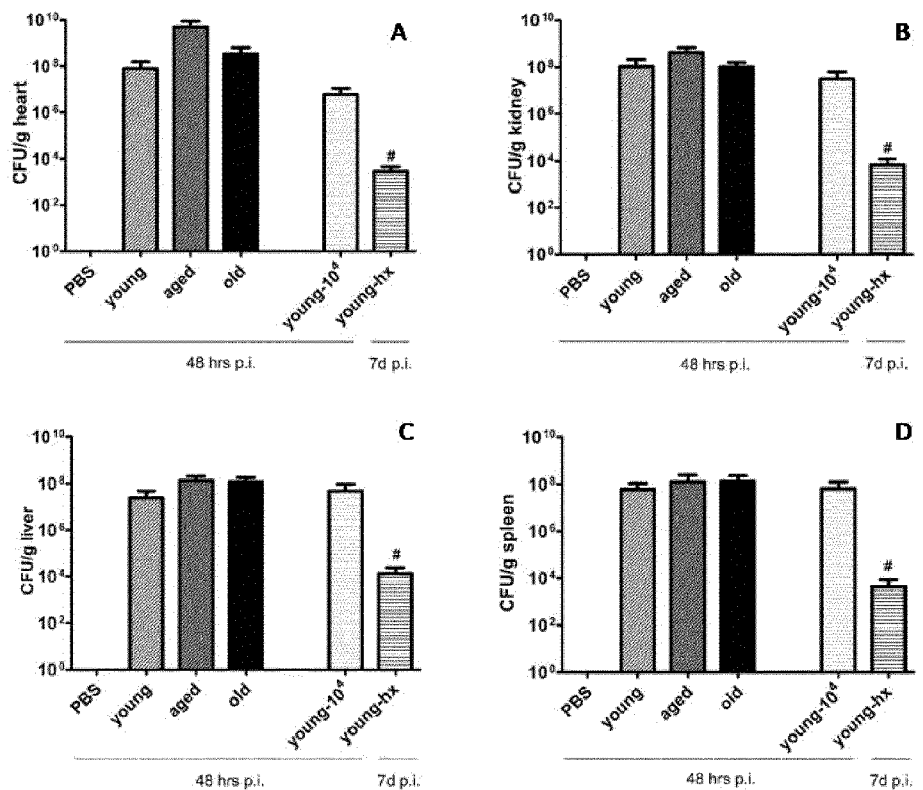
FIG. 7 (FIGS. 7A-7D): Bacterial load of distant organs. Colony forming units (CFU) of *E. coli* expressed per gram organ were counted after overnight incubation after sacrifice at 48 hours after uterine ligation and inoculation (p.i.) of $10^3$ CFU of *E. coli* in young, aged and old mice, or of $10^4$ CFU in young mice (young-$10^4$), or at 7 days p.i. of $10^4$ CFU in mice which underwent removal of the inoculated uterus at 48 hours p.i. (young-hx). Mice inoculated with PBS had negative bacterial culture results. The combined results of independent experiments are shown (n=15 for each group inoculated with *E. coli*, and n=5-7 for mice inoculated with PBS). Data are means±SEM. *, $p<0.05$ and **, $p<0.01$ compared to age-matched PBS controls; #, $p<0.05$ compared to young-$10^4$ mice. Specifically and as indicated on their respective y-axes, FIG. 7A concerns the heart, FIG. 7B concerns the kidney, FIG. 7C concerns the liver, and FIG. 7D concerns the spleen.

In analogy with the staging criteria of the Acute Kidney Injury Network (AKIN) or Risk-Injury-Failure stages of the RIFLE criteria (Bellomo et al., 2004; Mehta et al., 2007), renal dysfunction in mice was classified in 3 stages based on serum creatinine (sCr). Since baseline sCr concentrations (before inoculation) were not available for each individual mouse, the increase of sCr was described compared to the mean sCr concentrations of PBS-inoculated controls at 48 hrs p.i. (i.e., 0.18 mg/dl). Serum creatinine and blood urea nitrogen (BUN) concentrations, as well as the tubular damage score (TDS) were not significantly different between PBS-inoculated controls of the three age categories. Renal dysfunction was documented by increased concentrations of sCr and BUN in infected mice compared to PBS-inoculated mice. Moreover, these concentrations were significantly higher at 48 hrs than at 24 hrs p.i. of *E. coli* (p<0.05). In addition, kidney histological changes with predominantly tubular cell vacuolization were observed in aged, old and young-$10^4$ mice at 48 hrs p.i. of *E. coli* (FIG. 6). The TDS was not significantly different between young animals inoculated with $10^3$ CFU and young PBS-inoculated controls. Although the percentage of damaged areas (TDS) did not significantly differ between young-$10^4$, aged and old mice, the tubular lesions in young-$10^4$ were less severe. TDS was moderately correlated with sCr concentrations and proposed cut-offs for AKIN-like staging criteria (r=0.64 and 0.66, respectively, p<0.01). Serum creatinine concentrations and TDS of young-hx mice at day 7 p.i. were significantly lower than concentrations or scores of young-$10^4$ mice at 48 hrs p.i. When all mice with AKI-ARF (acute renal failure) as defined by the described criteria, across the different age categories were grouped and compared with mice which did not develop AKI at 48 hrs p.i., TDS, sCr, BUN, CFU/g organ, IL-6, TNF, KC but not IL-10, MCP-1 and nitrite were significantly higher in mice with AKI-ARF. Temperature at 48 hrs p.i. was significantly lower in mice with AKI-ARF than without. TDS, temperature and BUN were not significantly different between PBS-inoculated controls and mice without AKI, while the other parameters were.

(ii) Western Blot Analysis Reveals Activation of Caspase-1, -3 and -7 in Septic Young, Aged and Old Mice with AKI Activation of caspase-1, -3 and -7 was detected in kidney lysates of infected mice classified with AKI-ARF (AKIN 2 or 3), and with TDS>2, but not in PBS-inoculated controls or in mice at risk of renal dysfunction (Risk, AKIN 1) or with TDS≤2. Caspase-3 but not caspase-1 or -7 was also activated in kidney lysates of old mice inoculated with PBS (FIG. 6A). TUNEL assay confirmed that tubular cell apoptosis was a prominent feature of AKI at 48 hrs p.i. of *E. coli* (FIG. 6B).

Figure 5:
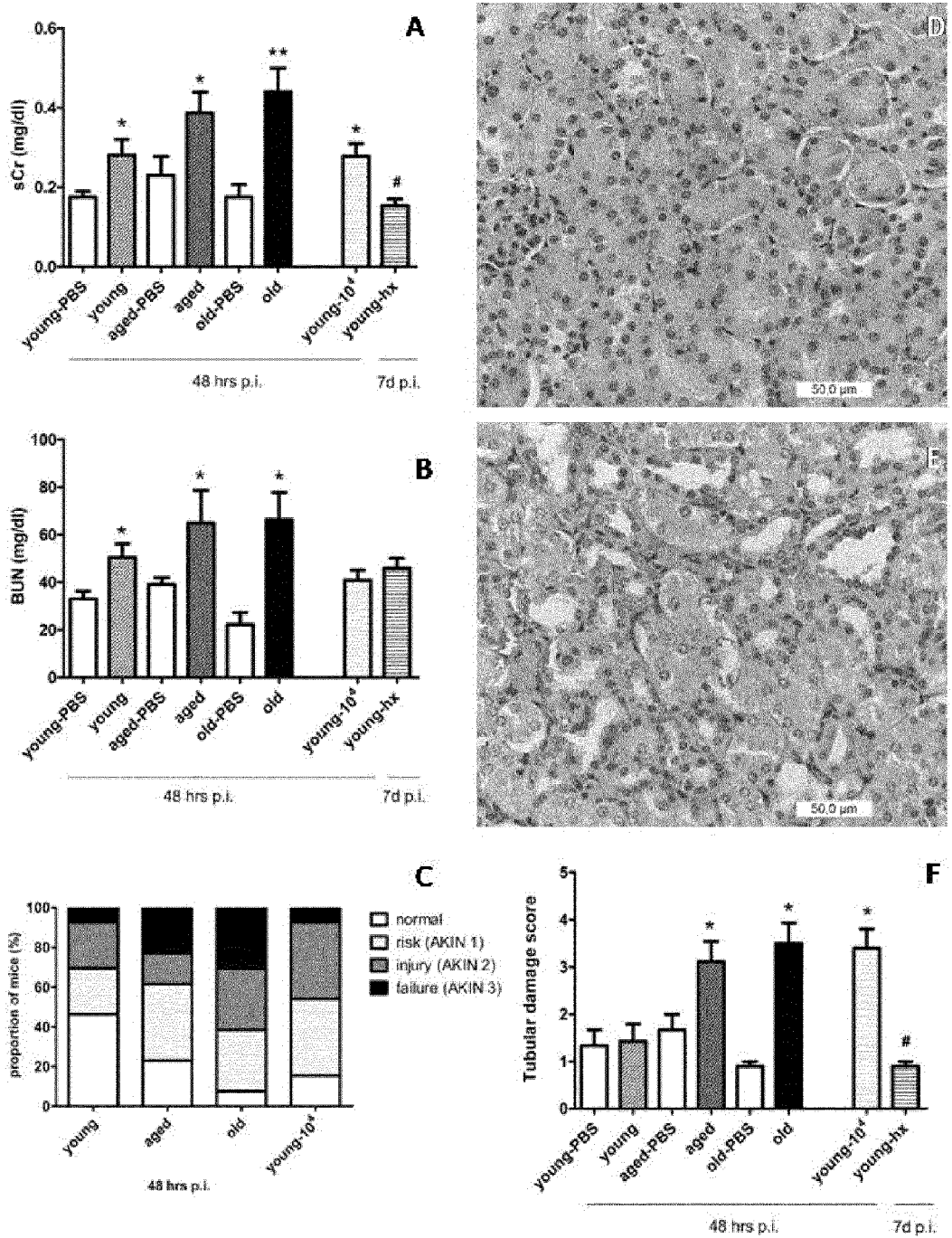
FIG. 5: Serum creatinine (sCr) and blood urea nitrogen (BUN) concentrations, with renal histological changes. Concentrations of sCr (A) and BUN (B) at 48 hours after inoculation (p.i.) of $10^3$ CFU of *E. coli* or PBS in young, aged and old mice, or with $10^4$ CFU in young mice (young-$10^4$), and at 7 days (d) p.i. with $10^4$ CFU in young mice which underwent removal of the infected uterus (young-hx). (C) AKIN- and RIF(LE)-like criteria; normal, sCr<0.27 mg/dl; risk (R) of renal dysfunction (AKIN 1), 0.27-0.35 mg/dl; injury (I) of the kidney (AKIN 2), 0.36-0.54 mg/dl; and failure (F) of renal function (AKIN 3), >0.54 mg/dl. Representative renal histological damage at 48 hours p.i. with PBS (D) or *E. coli* (vacuolization of tubular cells) (E). Kidney sections are stained with hematoxylin-eosin, original magnification, ×400. The tubular damage score (TDS, see Materials and Methods section) quantifies the degree of kidney injury (F). Combined results of independent experiments are shown (n=15 per group inoculated with *E. coli*, and n=5-7 per group inoculated with PBS). Data are mean±SEM. *, $p<0.05$ and **, $p<0.01$ compared to age-matched PBS controls; #, $p<0.05$ compared to young-$10^4$ mice.

Uterine Ligation and Inoculation of *E. Coli* in Aged Mice Results in Sepsis with and without AKI 1) Variation in Renal Response after Septic Insult Renal histological changes consistent with AKI, such as tubular cell vacuolization (Miyaji et al.; 2003; Doi et al., 2008) and a significantly higher TDS were found in some mice at $T_1$ after inoculation with *E. coli* (n=5/12). Other infected mice had no light microscopic features of AKI at $T_1$ (n=7/12), nor was their TDS significantly different from PBS-inoculated mice. Consequently, septic mice were subdivided as only septic (S) or septic with AKI (S+AKI). Renal dysfunction was documented by significantly increased concentrations of sCr and BUN in S+AKI mice compared to S mice and PBS-inoculated mice. Urine output in S+AKI mice was significantly decreased at $T_1$ when compared to the output before inoculation ($T_0$) and to the output of S mice at $T_1$ (FIG. 5i). In contrast to sCr, BUN and TDS, urinary albumin to urinary creatinine ratios and urinary albumin to urinary total protein ratios of S and S+AKI mice at $T_1$ were significantly increased compared to $T_0$ and to ratios of PBS-inoculated controls at $T_0$ and $T_1$.

2) Inflammation is More Severe in Septic Mice with AKI than without AKI

Hypothermia was present at $T_1$ in S+AKI mice, while the body temperature of S mice was not significantly different before ($T_0$) and after inoculation ($T_1$). The bacterial load of distant organs (CFU of *E. coli*/g organ) was significantly higher in S+AKI mice than in S mice. No bacteria were present in blood nor in organs of PBS-inoculated mice. Plasma IL-1β levels at $T_1$ were below the detection limit in all mice. Plasma concentrations of IL-6, IL-10, TNF, KC, and MCP-1 were significantly increased at $T_1$ in infected mice compared to PBS-inoculated mice. With the exception of IL-10, these were also significantly increased in S+AKI mice compared to S mice.

Discovery and Validation of Candidate Urinary Biomarkers for Sepsis-Induced AKI

1) Upregulated Excretion of Urinary Proteins after Experimental Sepsis

Three-hundred and one different proteins were identified in the combined urinary proteome of S and S+AKI mice ($T_1$), of which 129 were not detected in urine before infection ($T_0$). Eighty-six percent of these proteins were related to the cellular part, and 12% to the extracellular part (universal Gene Ontology (GO) annotation terms (Ashburner et al., 2000)). Results of the differential analysis of urinary proteomes at $T_0$ vs $T_1$ of S and S+AKI mice, and of S $T_1$ vs S+AKI $T_1$ are shown in Table 1.

TABLE 1

Results of the differential analysis of urinary proteomes: identified proteins.

| Numbers of proteins | S_$T_1$/$T_0$ | S + AKI_$T_1$/$T_0$ | S + AKI_$T_1$/S_$T_1$ |
|---|---|---|---|
| Identified | 327 | 346 | 280 |
| Present in 3 technical repeats | 119 | 155 | 98 |
| Present after manual confirmation of MS spectra | 101 | 133 | 87 |
| Range of protein ratios | 5000.1-1.2 | 714.3-0.2 | 20.6-0.2 |
| Proportion of proteins with ratio 0.5-2.0 | 1.0% | 4.5% | 67.8% |

TABLE 1-continued

Results of the differential analysis of urinary proteomes: identified proteins.

| Numbers of proteins | $S\_T_1/T_0$ | $S+AKI\_T_1/T_0$ | $S+AKI\_T_1/S\_T_1$ |
|---|---|---|---|
| Proportion of proteins with ratio <0.5 | 0% | 1.5% | 4.6% |

Legend:
Ratios are shown of proteins in urine collected before sepsis ($T_0$) and at 48 h after infection ($T_1$) from mice which were septic at $T_1$ (S) or were septic and developed sepsis-induced AKI at $T_1$ (S + AKI).

2) Marker Selection Process

Three different approaches of the differential analyses were performed to select candidate markers with a potential to identify sepsis with AKI and not sepsis without AKI. First, proteins with a $T_1/T_0$ ratio higher than 9.3 in S+AKI (n=79) were selected. This cut-off ratio was based on the ratio of major urinary protein 5 (MUP5). Because MUPs are abundantly present proteins with a pheromone function, and not expected to be upregulated after sepsis, these proteins and all proteins with a ratio lower than the MUPs were hypothetically excluded as candidate markers. In addition, 64 proteins were excluded from the selection process because they were exclusively identified in the S $T_1/T_0$ analysis (n=64/101). Finally, only proteins with a S+AKI $T_1$/S $T_1$>2.0 were taken into account for further selection (n=24/87). This first approach resulted in a list of 44 proteins, and a commercial antibody was available for 25 of these (Table 2). The second approach was based on the 71 proteins which were identified in both S+AKI $T_1/T_0$ and S $T_1/T_0$ and had a (S+AKI $T_1/T_0$)/(S $T_1$/To) ratio>1.0 (FIG. 3). The third approach selected 24 proteins with a ratio>2.0 in the S+AKI $T_1$/S $T_1$ analysis (Table 2). In total, 46 different proteins were now considered candidates markers for sepsis-induced AKI. The 8 proteins at the top of the ranking based on both ratios of S+AKI $T_1/T_0$ and S+AKI $T_1$/S $T_1$ were finally chosen for further validation by western blot analysis: neutrophil gelatinase-associated lipocalin (NGAL), thioredoxin (TRX), gelsolin, chitinase 3-like-3 (CHI3L3), sepiapterin reductase (SPR), osteopontin (OPN), cathepsin L1 (CATH L1), and uteroglobin (UT).

TABLE 2

Table 2. Candidate urinary biomarkers for sepsis-induced acute kidney injury: selection approaches based on quantitative gel-free proteomics data.

| | | $S+AKI\_T_1/S\_T_1$ | | | $S+AKI$ | | | $S$ | | |
|---|---|---|---|---|---|---|---|---|---|---|
| Protein | Accession number | Fold increase at $T_1$ in S+AKI compared to S | ID | Different peptides | Fold increase at $T_1$ compared to $T_0$ | ID | Different peptides | Fold increase at $T_1$ compared to $T_0$ | ID | Different peptides |
| Neutrophil gelatinase-associated lipocalin | P11672 | 3.7 | 38 | 5 | 714.3 | 22 | 4 | 120.9 | 16 | 3 |
| Uteroglobin | Q06318 | 5.5 | 16 | 3 | 400.0 | 13 | 3 | 59.7 | 5 | 1 |
| Osteopontin | B10923 | 5.3 | 179 | 13 | 17.2 | 167 | 13 | 35.0 | 73 | 10 |
| Thioredoxin | P10639 | 2.5 | 15 | 3 | 11.9 | 9 | 3 | 30 | 6 | 2 |
| Protein S100-A8 | P27005 | 20.6 | 6 | 1 | | | | | | |
| Parvalbumin alpha | P32848 | 17.7 | 32 | 11 | 212.8 | 43 | 12 | | | |
| Myoglobin | P04247 | 15.7 | 11 | 4 | 416.7 | 12 | 3 | | | |
| Annexin A1 | P10107 | 7.1 | 3 | 1 | 5.7 | 3 | 2 | | | |
| Lactotransferrin | P08071 | 4.3 | 3 | 2 | 8.0 | 5 | 3 | | | |
| Apolipoprotein A-I | Q00623 | 4.0 | 5 | 2 | 2.7 | 5 | 3 | | | |
| Peptidyl-prolyl cis-trans isomerase A | P17742 | 3.9 | 4 | 2 | 27.9 | 6 | 3 | | | |
| Meprin A subunit beta | Q61847 | 3.3 | 4 | 2 | | | | | | |
| Cathepsin D | P18242 | 3.1 | 4 | 2 | 23.1 | 4 | 2 | | | |
| Calbindin | P12658 | 3.1 | 6 | 1 | | | | | | |
| Ig kappa chain C region | P01837 | 2.4 | 11 | 4 | 14.4 | 20 | 4 | 14.7 | 13 | 5 |
| Ezrin | P26040 | 2.4 | 20 | 5 | 9.5 | 25 | 9 | 5000.1 | 11 | 6 |
| Gamma-glutamyltranspeptidase 1 | Q60928 | 2.4 | 19 | 4 | 15.2 | 13 | 5 | 14.1 | 7 | 3 |
| Lymphocyte antigen 6D | P35459 | 2.4 | 7 | 1 | 11.6 | 9 | 1 | 43.1 | 4 | 1 |
| Na(+)/H(+) exchange regulatory cofactor NHE-RF3 | Q9JIL4 | 2.4 | 6 | 3 | 10.5 | 13 | 5 | 6.8 | 12 | 6 |
| Insulin-like growth factor-binding protein 7 | Q61581 | 2.3 | 5 | 1 | 11.3 | 4 | 2 | | | |
| Serotransferrin | Q92111 | 2.3 | 85 | 13 | 18.0 | 89 | 18 | 38.3 | 37 | 12 |
| Vitamin D-binding protein | P21614 | 2.2 | 13 | 5 | 25.0 | 13 | 7 | 37.9 | 11 | 6 |
| Alpha-enolase | P17182 | 2.1 | 9 | 5 | 14.5 | 11 | 5 | | | |
| Transthyretin | P07309 | 2.1 | 6 | 1 | 6.1 | 15 | 4 | 18.1 | 5 | 1 |
| *Sepiapterin reductase* | *Q64105* | | | | *35.5* | *3* | *1* | | | |
| *Gelsolin* | *P13020* | | | | *34.5* | *5* | *2* | | | |
| *Cathepsin L1* | *P06797* | | | | *24.8* | *5* | *2* | | | |
| *Chitinase-3-Like-3* | *O35744* | | | | *21.6* | *9* | *3* | | | |
| *Lipopolysaccharide-binding protein* | *Q61805* | | | | *117.6* | *3* | *1* | | | |
| *Complement C3* | *P01027* | | | | *19.6* | *12* | *8* | | | |
| *Serotransferrin* | *Q92111* | *2.3* | *85* | *13* | *18.0* | *89* | *18* | *38.3* | *37* | *12* |
| *N-acetylglucosamine-6-sulfatase* | *Q8BFR4* | | | | *18.2* | *9* | *5* | | | |
| *Prothymosin alpha* | *P26350* | | | | *15.7* | *3* | *1* | | | |
| *Kininogen-1* | *O08677* | *1.2* | *11* | *5* | *13.7* | *8* | *6* | | | |
| *Annexin A5* | *P48036* | | | | *13.0* | *10* | *3* | | | |
| *Beta-2-microglobulin* | *P01887* | | | | *11.5* | *3* | *1* | | | |
| *kinesin-associated protein 3* | *P70188* | | | | *10.7* | *4* | *1* | | | |

TABLE 2-continued

Table 2. Candidate urinary biomarkers for sepsis-induced acute kidney injury: selection approaches based on quantitative gel-free proteomics data.

| | | S + AKI_$T_1$/S_$T_1$ | | | S + AKI | | | S | | |
|---|---|---|---|---|---|---|---|---|---|---|
| Protein | Accession number | Fold increase at $T_1$ in S + AKI compared to S | ID | Different peptides | Fold increase at $T_1$ compared to $T_0$ | ID | Different peptides | Fold increase at $T_1$ compared to $T_0$ | ID | Different peptides |
| *Destrin* | *Q9R0P5* | | | | 10.4 | 3 | 1 | | | |
| *Heat shock cognate 71 kDa protein* | *P63017* | | | | 9.8 | 4 | 2 | | | |

Legend:
Accession numbers of identified proteins are shown, as described in the Uniprot database.
Data of the quantitative comparison of proteomes of urine collected before sepsis ($T_0$) and at 48 h after infection ($T_1$) from mice which were septic at $T_1$ (S) or were septic and developed sepsis-induced AKI at $T_1$ (S + AKI).
Data are shown from proteins selected through the first approach (italics), third approach (normal) and both in the first and third approach (bold).
Some fields are blank because the protein was not detected in all 3 technical repeats and data were thus not used for marker selection approaches.
ID: number of identified peptides; different peptides: number of different identified peptides.

3) Preclinical Validation in Urine, Serum and Renal Tissue Homogenates of Mice

Figure 11:
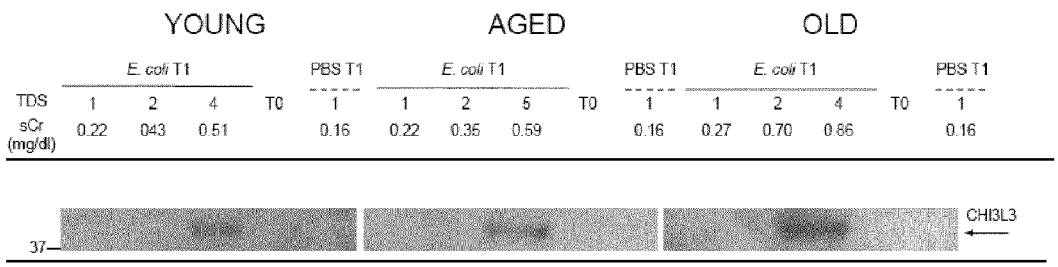
FIG. 11: Western blot analysis of chitinase 3-like-3 and sepiapterin reductase in individual mouse urine samples and renal tissue homogenates. Representative samples of young (12 to 14 weeks), aged (46 to 48 weeks) and old (70 to 72 weeks) female C57BL/6 mice were investigated for the presence chitinase 3-like protein 3 (CHI3L3) and sepiapterin reductase (SPR) in urine and in kidney lysates. Septic mice of different ages were defined with AKI when renal histology lesions consistent with AKI, tubular damage score (TDS)≥2 and serum creatinine (sCr) >0.24 mg/dl were present. Western blot results are shown of urine from mice infected with *E. coli*, before ($T_0$) and 48 hours after inoculation ($T_1$), as well as from control mice after PBS-inoculation ($T_1$). Specifically, the top figure is a western blot analysis of chitinase 3-like-3 in individual mouse urine samples. The middle figure (indicated as "A" in FIG. 11) is a western blot analysis of chitinase 3-like-3 in individual mouse renal tissue homogenates. The bottom figure (indicated as "B" in FIG. 11) is a western blot analysis of sepiapterin reductase in individual mouse urine samples and renal tissue homogenates.
Figure 11:
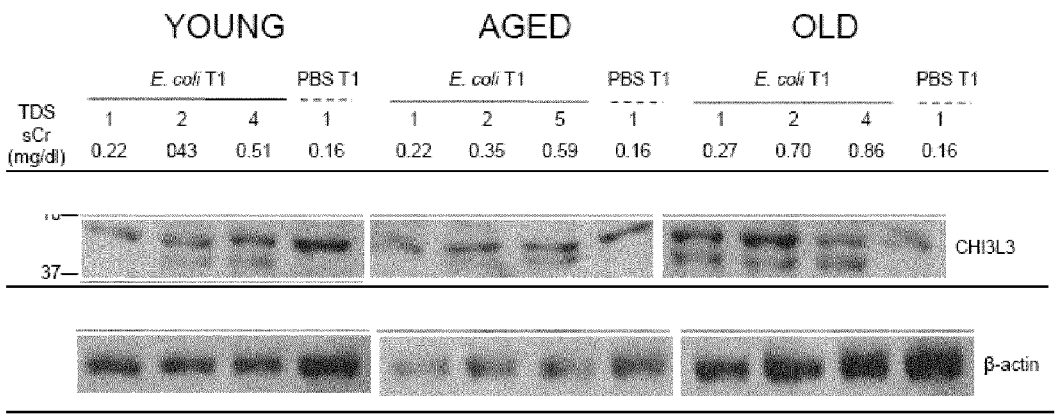
Figure 11:
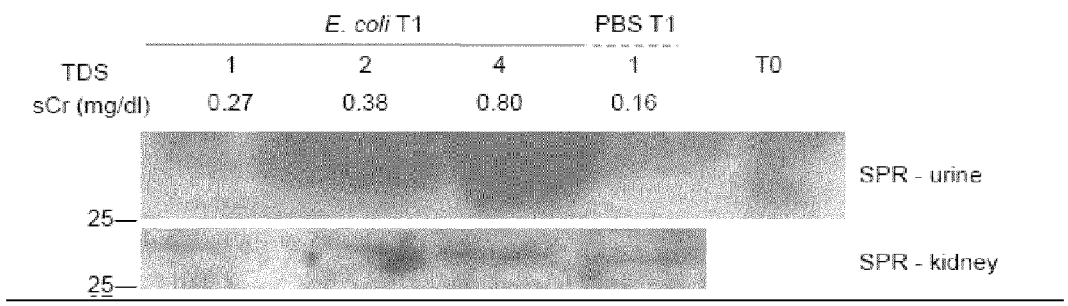

Septic mice of different ages were defined with AKI when renal histology lesions consistent with AKI, TDS≥2 and sCr>0.24 mg/dl were present. The cut-off for sCr was chosen based on a 1.5 fold increase in sCr compared to the mean sCr of PBS-inoculated mice (i.e., 0.16 mg/dl), in analogy with the Acute Kidney Injury Network staging criteria for human AKI (Mehta et al., 2007). The differential presence of proteins was confirmed by western blot analysis of individual urine samples after PBS-inoculation ($T_1$), before septic insult ($T_0$) and of mice with and without septic AKI at $T_1$ (FIGS. 11A, 11C). Urinary CHI3L3 was only detected in septic mice with AKI (FIG. 11A). Urine of septic mice with AKI contained higher amounts of SPR (FIG. 11C) than urine of PBS-inoculated mice, septic mice without AKI, and mice recovering from sepsis after removal of the infected uterine horn (FIG. 11C).

To examine if the selected candidate biomarkers for sepsis-induced AKI originated from the kidney, western blot analyses were repeated on renal tissue homogenates (FIG. 11B). Two bands of CHI3L3 were observed in septic mice with AKI.

Figure 12:
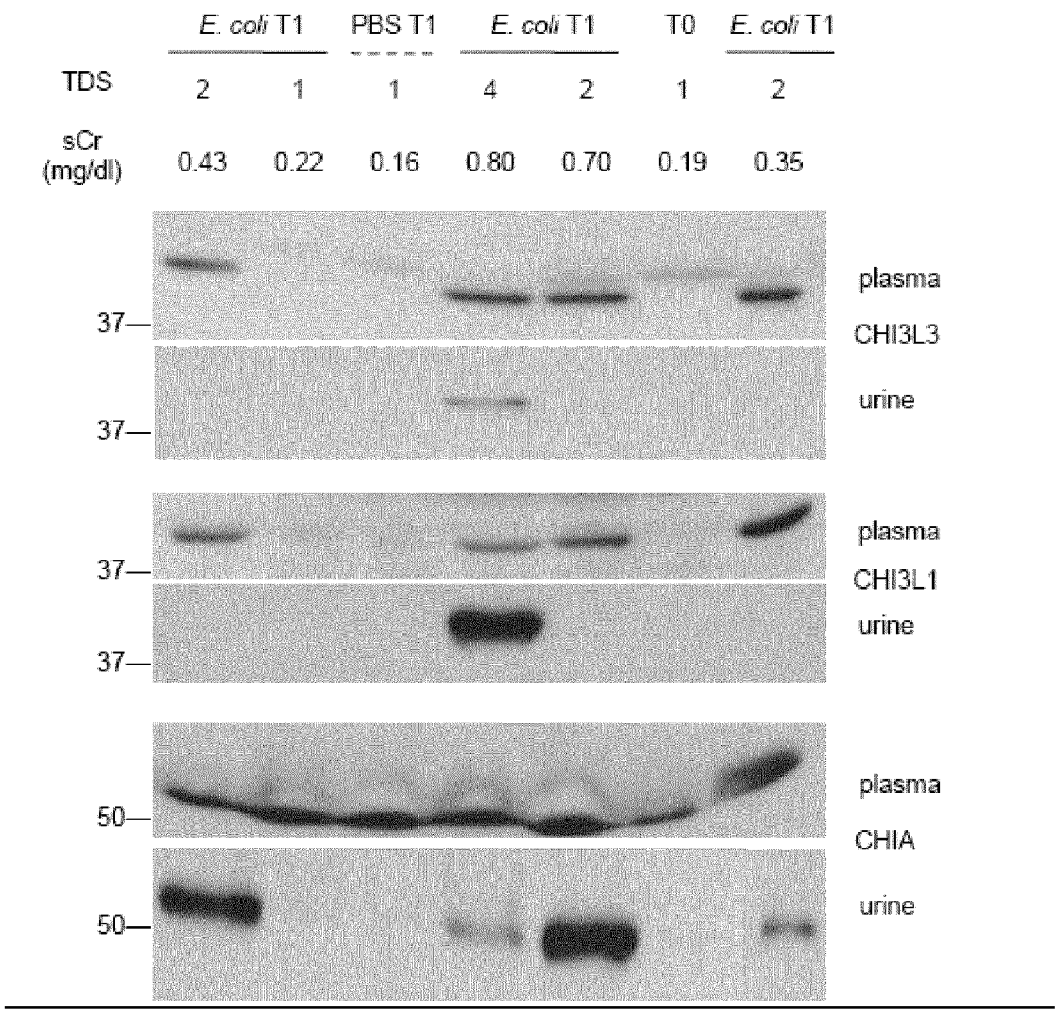
FIG. 12: Western blot analysis of chitinase 3-like-3 and -1, and acidic mammalian chitinase in individual mouse urine and plasma samples. Representative samples of female C57BL/6 mice were investigated for the presence of chitinase 3-like protein 3 and -1 (CHI3L3, CHI3L1), and acidic mammalian chitinase (CHIA) in urine and plasma. Septic mice were defined with AKI when renal histology lesions consistent with AKI, tubular damage score (TDS)≥2 and serum creatinine (sCr)>0.24 mg/dl were present. Western blot results are shown of urine from mice infected with *E. coli*, before ($T_0$) and 48 hours after inoculation ($T_1$), as well as from control mice after PBS-inoculation ($T_1$).

Because CHI3L3 was the most specific marker for sepsis-induced AKI, its presence in plasma was examined by western blot analysis (FIG. 12).

Figure 13:
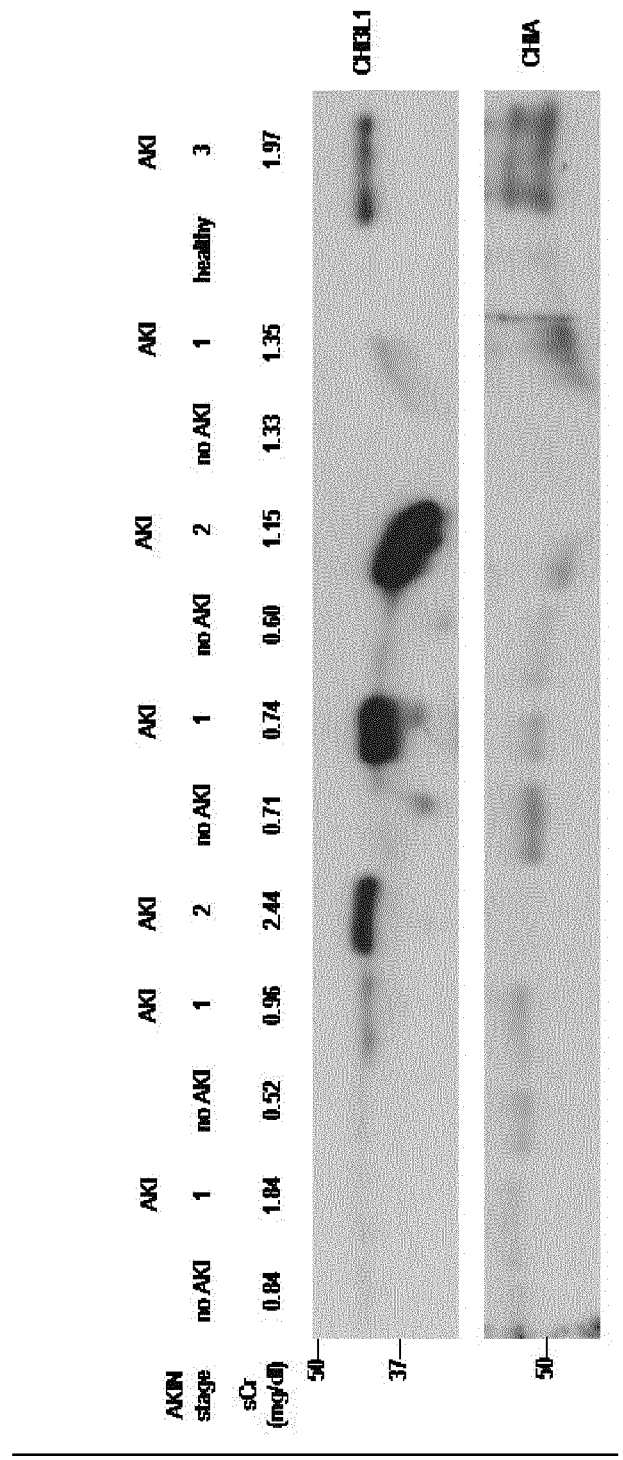
FIG. 13: Western blot analysis of chitinase 3-like-1 and acidic mammalian chitinase in urine samples from human septic patients. Representative samples of human septic patients were investigated for the urinary presence of chitinase 3-like protein 1 (CHI3L1) and acidic mammalian chitinase (CHIA). Patients were diagnosed with AKI and classified according to the AKIN criteria (Mehta et al., 2007) (upper row of the table: AKIN stage—lower row: serum creatinine (sCr) concentrations).
Figure 14:
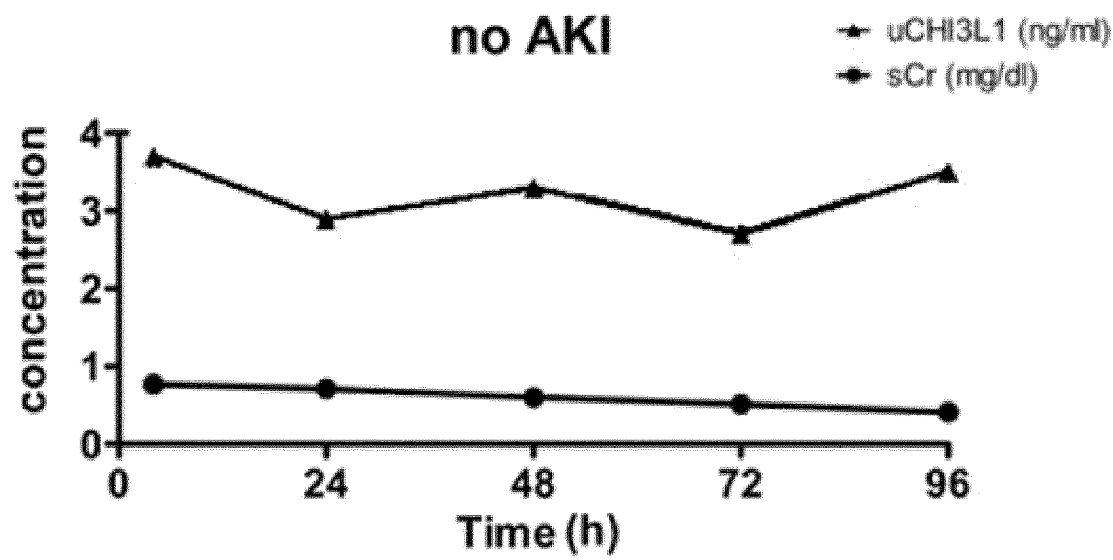
FIG. 14: ELISA of chitinase 3-like protein 1 in urine samples from human septic patients. Representative samples of human septic patients were investigated for the urinary presence of chitinase 3-like protein 1 (CHI3L1). Patients were diagnosed with AKI and classified according to the AKIN criteria (Mehta et al., 2007) (AKIN stage 0 or 1, serum creatinine (sCr) concentrations). Concentration-time profiles of routine (sCr) versus novel biomarkers (CHI3L1) in sepsis patients, without (FIG. 14A) and with (FIG. 14B) acute kidney injury (AKI) are shown. Time (h): time in hours after admission to intensive care; the arrow indicates the time point at which sCr detects AKI; correction of uCHI3L1 (urinary CH3L1) for changes in urinary output by normalization to uCr gives identical profiles; range of novel biomarker uCHI3L1 in healthy individuals: 0.2-0.9 ng/ml.
Figure 14:
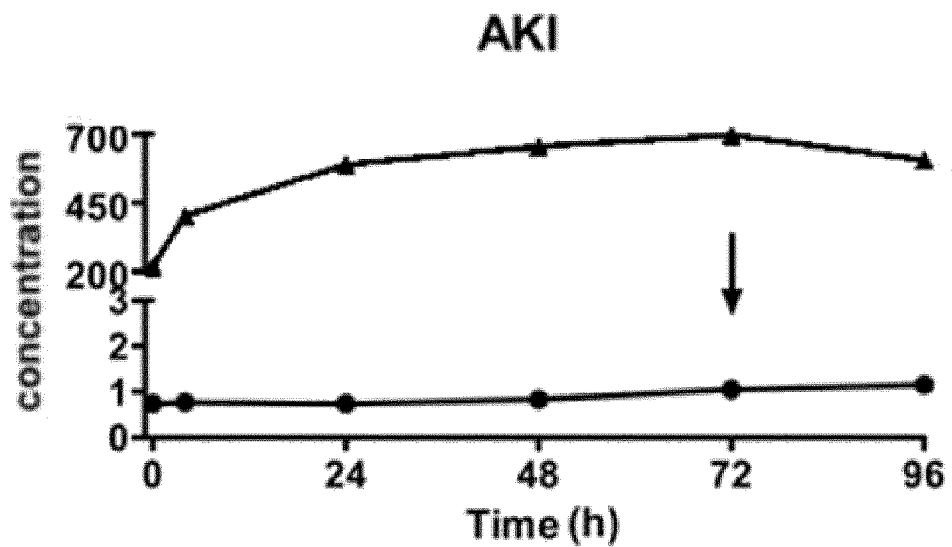

4) Preliminary Clinical Validation of Urinary CHI3L1 and CHIA in Human Septic Patients with and without AKI Murine CHI3L3 is structurally related to the human chitinase proteins and has considerable sequence homology with human CHI3L1 (Jin et al., 1998; Guo et al., 2000). Human CHI3L1 shares 73% amino acid sequence identity with mouse CHI3L1 and both were examined in urine of humans and mice, respectively. Another protein member of the mammalian chitinase family is acidic mammalian chitinase (CHIA), which was detected in S+AKI $T_1$/$T_0$ in a ratio of 7.0, and not in the technical repeats of S $T_1$/$T_0$. Because of its ratio<9.3 (MUP5), it was formerly not selected as candidate marker. Based on the promising results of the other members of the chitinase family, we examined the potential of both urinary CHI3L1 and CHIA as marker for sepsis-induced AKI in mouse and human samples by western blot analysis (FIGS. 12 and 13). Additionally, CHI3L1 was also analyzed with ELISA in these samples (FIG. 14).

C) Urine Proteome Profile of Aged Mice Before Septic Insult

Non-differential analysis of urine resulted in the identification of 210 different proteins, thereby expanding the current knowledge of the mouse urinary proteome. Proteins involved in cell proliferation, activation of immune response and platelets, and B cell receptor and TNF-mediated signaling (GO terms in biological processes) were present in the urinary proteome of sepsis with AKI (S+AKI) mice at $T_0$ but not in that of septic (S) mice at $T_0$. Differential analysis of the urine proteomes before infection revealed that 92 of 123 proteins were more abundantly present in mice which developed AKI after sepsis (S+AKI mice). These proteins were functionally categorized in the above mentioned processes and more specifically (subcategorization) in cellular apoptosis, endothelial cell proliferation, leukocyte migration, lymphocyte activation and differentiation, macrophage cytokine production, and wound healing.

REFERENCES

Barrera G, Landoni V, Martire-Greco D, et al. A model of polymicrobial peritonitis that induces the proinflammatory and immunosuppressive phases of sepsis. Infect Immun 2010, doi:10.1128/IA1.01127-10.

Bellomo R, Ronco C, Kellum J A, et al. Acute renal failure—definition, outcome measures, animal models, fluid therapy and information technology needs: the second international consensus conference of the acute dialysis quality initiative (ADQI) group. Crit. Care 2004; 8:R204-R212.

Buras J A, Holzmann B, Sitkovsky M. Animal models of sepsis: setting the stage. Nature reviews on cancer 2005; 10:854-865.

Deitch E A. Animal models of sepsis and shock: a review and lessons learned. Shock 1998; 9:1-11.

Dejager L, Pinheiro I, Dejonckheere E, et al. Cecal ligation and puncture: the gold standard model for polymicrobial sepsis? Trends in Microbiology 2011; 19(4):1-11.

Devarajan P. Review: neutrophil gelatinase-associated lipocalin: a troponin-like biomarker for human acute kidney injury. Nephrology 2010; 15:419-428.

Doi K, Leelahavanichkul A, Hu X, et al. Pre-existing renal disease promotes sepsis-induced acute kidney injury and worsens sepsis outcome via multiple pathways. Kidney Int 2008; 74:1017-1025.

Doi K, Leelahavanichkul A, Yuen P S T, et al. Animal models of sepsis and sepsis-induced kidney injury. J Clin Invest 2009; 119:2868-2878.

Dyson A, Singer M. Animal models of sepsis: why does preclinical efficacy fail to translate to the clinical setting? Crit. Care Med 2009; 37:S30-S37.

Faubel S, Ljubanovic D, Reznikov L, et al. Caspase-1-deficient mice are protected against cisplatin-induced apoptosis and acute tubular necrosis. Kidney Int 2004; 66:2202-2213.

Fink M P. Animal models of sepsis and its complications. Kidney Int 2008; 74:991-993.

Fonseca Ruiz N J, Cuesta Castro D P, Mesa Guerra A M, et al. Renal injury study in critical ill patients in accordance with the new definition given by the Acute Kidney Injury Network. Journal of critical care 2010.

Haase M, Haase-Fielitz A, Bellomo R, Mertens R. Neutrophil gelatinase-associated lipocalin as marker of acute renal disease. Curr Opin Hematol 18:11-18. 2011.

Holly M K, Dear J W, Hu X, et al. Biomarker and drug target discovery using proteomics in a new rat model of sepsis-induced acute renal failure. Kidney Int 2006; 70:496-506.

Hoste E A J, Lameire N H, Vanholder R C, et al. Acute renal failure in patients with sepsis in a surgical ICU: predictive factors, incidence, comorbidity and outcome. J Am Soc Nephrol 2003; 14:1022-1030.

Hubbard W J, Choudhry M, Schwacha M G, et al. Cecal ligation and puncture. Shock 2005; 24, Suppl 1:52-57.

Klenzak J, Himmelfarb J. Sepsis and the kidney. Crit. Care Clin 2005; 21:211-222.

Langenberg C, Bagshaw S M, May C N, et al. The histopathology of septic acute kidney injury: a systematic review. Crit. Care 2008; 12:R38-R45.

Lever A, Mackenzie I. Sepsis: definition, epidemiology, and diagnosis. BMJ 2007; 335:879-883.

Levy M M, fink, MP, Marshal J C, et al. 2001 SCCM/ESICM/ACCP/ATS/SIS international sepsis definitions conference. Crit. Care Med 2003; 31:1250-1256.

Lopes J A, Jorge S, Resina C, et al. Acute kidney injury in patients with sepsis: a contemporary analysis. J Infect Dis 2009; 13:176-191.

Maier S, Traeger T, Entleutner M, et al. Cecal ligation and puncture versus colon ascendens stent peritonitis: two distinct animal models for polymicrobial sepsis. Shock 2004; 21:505-511.

Martensson J, Bell M, Oldner A, Xu S, Venge P, Martling C R. Neutrophil gelatinase-associated lipocalin in adult septic patients with and without acute kidney injury. Intensive Care Med 2010; 36:1333-1340.

Mehta R L, Bouchard J, Soroko S B, et al. Sepsis as a cause and consequence of acute kidney injury: Program to Improve Care in Acute Renal Disease. Intensive Care Med 2011; 37:241-28.

Mehta R L, Kellum J A, Shah S V, et al. Acute kidney injury network: report of an initiative to improve outcomes in acute kidney injury. Crit. Care 2007; 11:R31.

Miyaji T, Hu X, Yuen P S T, et al., Ethyl pyruvate decreases sepsis-induced acute renal failure and multiple organ damage in aged mice. Kidney Int 2003; 64:1620-1631.

Neild G H. Multi-organ renal failure in the elderly. Int Urol Nephrol 2001; 32:559-565.

Nejat M, Pickering J W, Walker R J, Westhuyzen J, Shaw G M, Frampton C M, Endre Z H. Urinary cystatin C is diagnostic of acute kidney injury and sepsis, and predicts mortality in the intensive care unit. Crit. Care 2010; 14:R85

Poli-de-Figueiredo L Z, Gamido A G, Nakagawa N, et al. Experimental models of sepsis and their clinical relevance. Shock 2008; 30:S53-S59.

Rangel-Frausto M S, Pittet D, Costigan M, et al. the natural history of the systemic inflammatory response syndrome (SIRS). A prospective study. JAMA 1995; 273:117-123.

Reinhart K, Meisner M, Brunkhorst F M. Markers for sepsis diagnosis: what is useful? Crit. Care Clin 2006; 22:503-519.

Rittirsch D, Hoesel L M, Ward P A. The disconnect between animal models of sepsis and human sepsis. J Leuckoc Biol 2007; 81:137-143.

Russell J A, et al. Changing pattern of organ dysfunction in early human sepsis is related to mortality. Crit. Care Med 2000; 28:3405-3411.

Siew E D, Ikizler T A, Gebretsadik T, Shintani A, Wickersham N, Bossert F, Peterson J F, Parikh C R, May A K, Ware L B. Elevated urinary IL-18 levels at the time of ICU admission predict adverse clinical outcomes. Clin J Am Soc Nephrol 2010; 5:1497-1505.

Siew E D, Ware L B, Gebretsadik T, Shintani A, Moons K G M, Wickersham N, Bossert F, Ikizler T A. Urine neutrophil gelatinase-associated lipocalin moderately predicts acute kidney injury in critically ill adults. J Am Soc Nephrol 2009; 20:1823-1832.

Soni S S, Ronco C, Katz N, Cruz D N. Early diagnosis of acute kidney injury: the promise of novel biomarkers. Blood Purif 2009; 28:165-174.

Vincent J L, Sakr Y, Sprung C L, et al. Sepsis in European intensive care units: results of the SOAP study. Crit. Care Med 2006; 34:344-353.

Zanotti-Cavazzoni S L and Goldfarb R D. Animal models of sepsis. Crit. Care Clin 2009; 25:703-719.

The invention claimed is:

1. A composition comprising:

binding molecules to chitinase 3-like protein 1, and urine from a subject;

wherein the subject is selected from the group consisting of:

a critically ill subject in intensive care, a subject suffering from septic shock, a subject post-operative from cardiac surgery, a critically ill subject suffering from burns, and/or trauma, and a subject who has ingested nephrotoxic drugs or radiocontrast agents.

2. The composition of claim 1, wherein the chitinase-3-like protein 1 comprises SEQ ID NO:1.

* * * * *

SEQUENCE LISTING

```
<160> NUMBER OF SEQ ID NOS: 4

<210> SEQ ID NO 1
<211> LENGTH: 383
<212> TYPE: PRT
<213> ORGANISM: Homo sapiens

<400> SEQUENCE: 1

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
        50                  55                  60
```

```
His Ile Asp Thr Trp Glu Trp Asn Asp Val Thr Leu Tyr Gly Met Leu
 65                  70                  75                  80

Asn Thr Leu Lys Asn Arg Asn Pro Asn Leu Lys Thr Leu Leu Ser Val
                 85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 2
<211> LENGTH: 476
<212> TYPE: PRT
<213> ORGANISM: Homo sapiens

<400> SEQUENCE: 2

Met Thr Lys Leu Ile Leu Leu Thr Gly Leu Val Leu Ile Leu Asn Leu
  1               5                  10                  15

Gln Leu Gly Ser Ala Tyr Gln Leu Thr Cys Tyr Phe Thr Asn Trp Ala
                 20                  25                  30

Gln Tyr Arg Pro Gly Leu Gly Arg Phe Met Pro Asp Asn Ile Asp Pro
            35                  40                  45

Cys Leu Cys Thr His Leu Ile Tyr Ala Phe Ala Gly Arg Gln Asn Asn
        50                  55                  60
```

```
Glu Ile Thr Thr Ile Glu Trp Asn Asp Val Thr Leu Tyr Gln Ala Phe
 65                  70                  75                  80

Asn Gly Leu Lys Asn Lys Asn Ser Gln Leu Lys Thr Leu Leu Ala Ile
                 85                  90                  95

Gly Gly Trp Asn Phe Gly Thr Ala Pro Phe Thr Ala Met Val Ser Thr
            100                 105                 110

Pro Glu Asn Arg Gln Thr Phe Ile Thr Ser Val Ile Lys Phe Leu Arg
        115                 120                 125

Gln Tyr Glu Phe Asp Gly Leu Asp Phe Asp Trp Glu Tyr Pro Gly Ser
    130                 135                 140

Arg Gly Ser Pro Gln Asp Lys His Leu Phe Thr Val Leu Val Gln
145                 150                 155                 160

Glu Met Arg Glu Ala Phe Glu Gln Glu Ala Lys Gln Ile Asn Lys Pro
            165                 170                 175

Arg Leu Met Val Thr Ala Ala Val Ala Ala Gly Ile Ser Asn Ile Gln
        180                 185                 190

Ser Gly Tyr Glu Ile Pro Gln Leu Ser Gln Tyr Leu Asp Tyr Ile His
    195                 200                 205

Val Met Thr Tyr Asp Leu His Gly Ser Trp Glu Gly Tyr Thr Gly Glu
210                 215                 220

Asn Ser Pro Leu Tyr Lys Tyr Pro Thr Asp Thr Gly Ser Asn Ala Tyr
225                 230                 235                 240

Leu Asn Val Asp Tyr Val Met Asn Tyr Trp Lys Asp Asn Gly Ala Pro
            245                 250                 255

Ala Glu Lys Leu Ile Val Gly Phe Pro Thr Tyr Gly His Asn Phe Ile
        260                 265                 270

Leu Ser Asn Pro Ser Asn Thr Gly Ile Gly Ala Pro Thr Ser Gly Ala
    275                 280                 285

Gly Pro Ala Gly Pro Tyr Ala Lys Glu Ser Gly Ile Trp Ala Tyr Tyr
290                 295                 300

Glu Ile Cys Thr Phe Leu Lys Asn Gly Ala Thr Gln Gly Trp Asp Ala
305                 310                 315                 320

Pro Gln Glu Val Pro Tyr Ala Tyr Gln Gly Asn Val Trp Val Gly Tyr
            325                 330                 335

Asp Asn Ile Lys Ser Phe Asp Ile Lys Ala Gln Trp Leu Lys His Asn
        340                 345                 350

Lys Phe Gly Gly Ala Met Val Trp Ala Ile Asp Leu Asp Asp Phe Thr
    355                 360                 365

Gly Thr Phe Cys Asn Gln Gly Lys Phe Pro Leu Ile Ser Thr Leu Lys
370                 375                 380

Lys Ala Leu Gly Leu Gln Ser Ala Ser Cys Thr Ala Pro Ala Gln Pro
385                 390                 395                 400

Ile Glu Pro Ile Thr Ala Ala Pro Ser Gly Ser Gly Asn Gly Ser Gly
            405                 410                 415

Ser Ser Ser Ser Gly Gly Ser Ser Gly Ser Gly Phe Cys Ala Val
        420                 425                 430

Arg Ala Asn Gly Leu Tyr Pro Val Ala Asn Asn Arg Asn Ala Phe Trp
    435                 440                 445

His Cys Val Asn Gly Val Thr Tyr Gln Gln Asn Cys Gln Ala Gly Leu
450                 455                 460

Val Phe Asp Thr Ser Cys Asp Cys Cys Asn Trp Ala
465                 470                 475
```

-continued

```
<210> SEQ ID NO 3
<211> LENGTH: 368
<212> TYPE: PRT
<213> ORGANISM: Homo sapiens

<400> SEQUENCE: 3

Met Val Ser Thr Pro Glu Asn Arg Gln Thr Phe Ile Thr Ser Val Ile
1               5                   10                  15

Lys Phe Leu Arg Gln Tyr Glu Phe Asp Gly Leu Asp Phe Asp Trp Glu
            20                  25                  30

Tyr Pro Gly Ser Arg Gly Ser Pro Gln Asp Lys His Leu Phe Thr
            35                  40                  45

Val Leu Val Gln Glu Met Arg Glu Ala Phe Glu Gln Glu Ala Lys Gln
    50                  55                  60

Ile Asn Lys Pro Arg Leu Met Val Thr Ala Ala Val Ala Ala Gly Ile
65                  70                  75                  80

Ser Asn Ile Gln Ser Gly Tyr Glu Ile Pro Gln Leu Ser Gln Tyr Leu
                85                  90                  95

Asp Tyr Ile His Val Met Thr Tyr Asp Leu His Gly Ser Trp Glu Gly
            100                 105                 110

Tyr Thr Gly Glu Asn Ser Pro Leu Tyr Lys Tyr Pro Thr Asp Thr Gly
        115                 120                 125

Ser Asn Ala Tyr Leu Asn Val Asp Tyr Val Met Asn Tyr Trp Lys Asp
    130                 135                 140

Asn Gly Ala Pro Ala Glu Lys Leu Ile Val Gly Phe Pro Thr Tyr Gly
145                 150                 155                 160

His Asn Phe Ile Leu Ser Asn Pro Ser Asn Thr Gly Ile Gly Ala Pro
                165                 170                 175

Thr Ser Gly Ala Gly Pro Ala Gly Pro Tyr Ala Lys Glu Ser Gly Ile
            180                 185                 190

Trp Ala Tyr Tyr Glu Ile Cys Thr Phe Leu Lys Asn Gly Ala Thr Gln
        195                 200                 205

Gly Trp Asp Ala Pro Gln Glu Val Pro Tyr Ala Tyr Gln Gly Asn Val
    210                 215                 220

Trp Val Gly Tyr Asp Asn Ile Lys Ser Phe Asp Ile Lys Ala Gln Trp
225                 230                 235                 240

Leu Lys His Asn Lys Phe Gly Gly Ala Met Val Trp Ala Ile Asp Leu
                245                 250                 255

Asp Asp Phe Thr Gly Thr Phe Cys Asn Gln Gly Lys Phe Pro Leu Ile
            260                 265                 270

Ser Thr Leu Lys Lys Ala Leu Gly Leu Gln Ser Ala Ser Cys Thr Ala
        275                 280                 285

Pro Ala Gln Pro Ile Glu Pro Ile Thr Ala Ala Pro Ser Gly Ser Gly
    290                 295                 300

Asn Gly Ser Gly Ser Ser Ser Gly Gly Ser Gly Ser Gly
305                 310                 315                 320

Phe Cys Ala Val Arg Ala Asn Gly Leu Tyr Pro Val Ala Asn Asn Arg
                325                 330                 335

Asn Ala Phe Trp His Cys Val Asn Gly Val Thr Tyr Gln Gln Asn Cys
            340                 345                 350

Gln Ala Gly Leu Val Phe Asp Thr Ser Cys Asp Cys Cys Asn Trp Ala
        355                 360                 365
```

```
<210> SEQ ID NO 4
<211> LENGTH: 261
<212> TYPE: PRT
<213> ORGANISM: Homo sapiens

<400> SEQUENCE: 4

Met Glu Gly Gly Leu Gly Arg Ala Val Cys Leu Leu Thr Gly Ala Ser
1               5                   10                  15

Arg Gly Phe Gly Arg Thr Leu Ala Pro Leu Leu Ala Ser Leu Leu Ser
            20                  25                  30

Pro Gly Ser Val Leu Val Leu Ser Ala Arg Asn Asp Glu Ala Leu Arg
        35                  40                  45

Gln Leu Glu Ala Glu Leu Gly Ala Glu Arg Ser Gly Leu Arg Val Val
    50                  55                  60

Arg Val Pro Ala Asp Leu Gly Ala Glu Ala Gly Leu Gln Gln Leu Leu
65                  70                  75                  80

Gly Ala Leu Arg Glu Leu Pro Arg Pro Lys Gly Leu Gln Arg Leu Leu
                85                  90                  95

Leu Ile Asn Asn Ala Gly Ser Leu Gly Asp Val Ser Lys Gly Phe Val
                100                 105                 110

Asp Leu Ser Asp Ser Thr Gln Val Asn Asn Tyr Trp Ala Leu Asn Leu
            115                 120                 125

Thr Ser Met Leu Cys Leu Thr Ser Ser Val Leu Lys Ala Phe Pro Asp
    130                 135                 140

Ser Pro Gly Leu Asn Arg Thr Val Val Asn Ile Ser Ser Leu Cys Ala
145                 150                 155                 160

Leu Gln Pro Phe Lys Gly Trp Ala Leu Tyr Cys Ala Gly Lys Ala Ala
                165                 170                 175

Arg Asp Met Leu Phe Gln Val Leu Ala Leu Glu Glu Pro Asn Val Arg
                180                 185                 190

Val Leu Asn Tyr Ala Pro Gly Pro Leu Asp Thr Asp Met Gln Gln Leu
            195                 200                 205

Ala Arg Glu Thr Ser Val Asp Pro Asp Met Arg Lys Gly Leu Gln Glu
    210                 215                 220

Leu Lys Ala Lys Gly Lys Leu Val Asp Cys Lys Val Ser Ala Gln Lys
225                 230                 235                 240

Leu Leu Ser Leu Leu Glu Lys Asp Glu Phe Lys Ser Gly Ala His Val
                245                 250                 255

Asp Phe Tyr Asp Lys
                260
```